United States Patent [19]

Schmidt et al.

[11] 3,982,011
[45] Sept. 21, 1976

[54] PENICILLINS
[75] Inventors: Gunter Schmidt; Karl Georg Metzger, both of Wuppertal, Germany
[73] Assignee: Bayer Aktiengesellschaft, Germany
[22] Filed: June 11, 1975
[21] Appl. No.: 585,890

Related U.S. Application Data
[62] Division of Ser. No. 419,950, Nov. 29, 1973, Pat. No. 3,931,153.

[30] Foreign Application Priority Data
Dec. 8, 1972 Germany.......................... 2260118

[52] U.S. Cl. ............................................. 424/271
[51] Int. Cl.² ............ C07D 499/68; C07D 499/70
[58] Field of Search.................. 260/239.1; 424/271

[56] References Cited
UNITED STATES PATENTS
3,268,513  8/1966  Grant et al....................... 260/239.1
3,433,784  3/1969  Long et al........................ 260/239.1

*Primary Examiner*—Gerald A. Schwartz

[57] ABSTRACT

Penicillins of the formula:

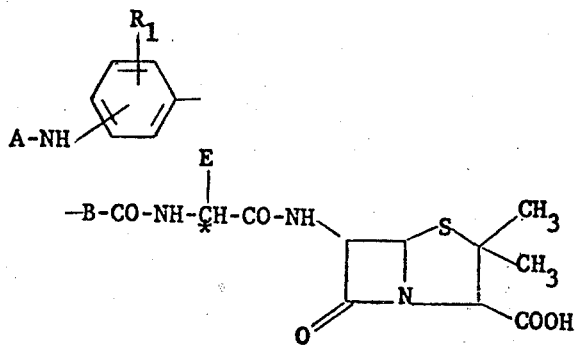

and their pharmaceutically acceptable nontoxic salts wherein
$R_1$ is hydrogen, halogen, lower alkyl, hydroxy, nitro or A—NH;
A is $R_2$,

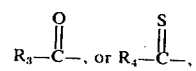

wherein
$R_2$ is hydrogen, lower alkyl or arylsulphenyl of 6 to 10 carbon atoms;
$R_3$ is hydrogen; lower alkyl; halo-(lower alkyl); cycloalkyl of 3 to 11 carbon atoms, unsubstituted or substituted by hydroxy or alkyl of 1 or 2 carbon atoms; cycloalkenyl of 3 to 11 carbon atoms; bicycloalkyl of up to 8 carbon atoms; bicycloalkenyl of up to 8 carbon atoms; aryl of 6 to 10 carbon atoms, unsubstituted or substituted by 1 to 3 substituents selected from the group consisting of alkyl of 1 to 4 carbon atoms, alkoxy of 1 to 4 carbon atoms, halogen, trifluoromethyl, nitro, amino, alkylsulphonyl of 1 to 4 carbon atoms, and methylenedioxy; azidoaryl of 6 to 10 carbon atoms, azido-(lower alkyl); amino; or thienyl;
$R_4$ is lower alkylamino or arylamino of 6 to 10 carbon atoms;
B is a direct bond; $CH_2$; $S-CH_2$; $CH=CH$; or $CO-NH-CH_2$;
E is phenyl or phenyl or thenyl, substituted by hydroxy, azido, lower alkyl, lower alkoxy, lower alkylthio or chlorine; and
C* is an asymmetric carbon atom, are useful for their antibacterial activity against both Gram-positive and Gram-negative bacteria.

21 Claims, No Drawings

PENICILLINS

This is a division of Ser. No. 419,950, filed Nov. 29, 1973, now U.S. Pat. No. 3,931,153.

The present invention relates to penicillins, to a process for their production, to pharmaceutical compositions useful for treating bacterial infections in humans and animals wherein said penicillins are the active agent, to the use of said penicillins as feedstuff additives and growth-promoting agents for use in mammals, poultry and fish, and to compositions comprising a nutritious material in combination with a growth-promoting or antibacterially effective amount of said penicillins.

It is known that substituted 6-(α-benzoylamino)acetamidopenicillanic acids which in the 3- or 4-position of the benzoyl radical carry a substituent derived from carbonic acid, of the formula:

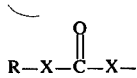

wherein
X is O or NH
can be synthesized; they are described in German Offenlegungsschrift No. 2,050,087.

On the other hand, those penicillin derivatives in which the amino groups in the ortho-, meta- or para-position of the benzoyl radical are not substituted by carbonic acid derivatives have not previously been disclosed.

More particularly, the present invention is concerned with penicillins of the formula:

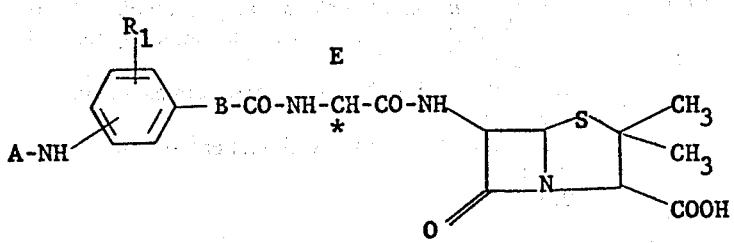

(I)

and pharmaceutically acceptable nontoxic salts thereof wherein
R₁ is hydrogen, halogen, lower alkyl, hydroxy, nitro or A—NH;
A is R₂,

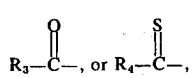

wherein
R₂ is hydrogen, lower alkyl or arylsulphenyl of 6 to 10 carbon atoms;
R₃ is hydrogen; lower alkyl; halo-(lower alkyl); cycloalkyl of 3 to 11 carbon atoms, unsubstituted or substituted by hydroxy or alkyl of 1 to 2 carbon atoms; cycloalkenyl of 3 to 11 carbon atoms; bicycloakyl of up to 8 carbon atoms; bicycloalkenyl of up to 8 carbon atoms; aryl of 6 to 10 carbon atoms, unsubstituted or substituted by 1 to 3 substituents selected from the group consisting of alkyl of 1 to 4 carbon atoms, alkoxy of 1 to 4 carbon atoms, halogen, trifluoromethyl, nitro, amino, alkylsulphonyl of 1 to 4 carbon atoms, and methylenedioxy; azidoaryl of 6 to 10 carbon atoms, azido-(lower alkyl); amino; or thienyl;
R₄ is lower alkylamino or arylamino of 6 to 10 carbon atoms;
B is a direct bond; CH₂; S—CH₂; CH=CH; or CO—NH—CH₂;
E is phenyl or phenyl or thenyl, substituted by hydroxy, azido, lower alkyl, lower alkoxy, lower alkylthio or chlorine; and
C* is an asymmetric carbon atom.

The asymmetric carbon atom C* gives rise to pairs of R- and S-diastereomers. The invention covers compounds of both diastereometric configurations both individually and in mixtures.

The preferred pharmaceutically acceptable nontoxic salts include: salts of the acid carboxyl group, such as the simple salts with sodium, potassium, magnesium, calcium, aluminum and ammonia, and the nontoxic substituted-ammonium salts with amines, such as di- and tri-lower alkylamines, procaine, dibenzylamine, N,N'-dibenzylethylenediamine, N-benzyl-β-phenylethylamine, N-methyl- and N-ethyl-morpholine, 1-ephenamine, dehydroabietylamine, N,N'-bis-dehydroabietylethylenediamine, N-lower alkylpiperidine and other amines which have already been used for forming salts of penicillins.

The phrase "lower alkyl" as used herein means a straight or branched chain alkyl moiety of 1 to 6 carbon atoms.

According to one embodiment of the present invention,

A is R₂,

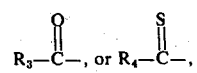

wherein
R₂ is hydrogen, lower alkyl or phenylsulphenyl;
R₃ is hydrogen; lower alkyl; halo-(lower alkyl); cycloalkyl of 3 to 11 carbon atoms, unsubstituted or substituted by hydroxy or alkyl of 1 to 2 carbon atoms; cycloalkenyl of 3 to 11 carbon atoms; bicycloalkyl of up to 8 carbon atoms; bicycloalkenyl of up to 8 carbon atoms; aryl of 6 to 10 carbon atoms, unsubstituted or substituted by 1 to 3 substituents selected from the group consisting of alkyl of 1 to 4 carbon atoms, alkoxy of 1 to 4 carbon atoms, halogen, trifluoromethyl, nitro, amino, alkylsulphonyl of 1 to 4 carbon atoms, and methylenedioxy; azidophenyl, azido-(lower alkyl); amino; or thienyl.

According to another embodiment of the present invention:

$R_1$ is A—NH and each

A is formyl, cyclopropylcarbonyl, or cyclobutylcarbonyl.

According to another embodiment of the present invention:

$R_2$ is hydrogen, lower alkyl or phenylsulphenyl;

$R_3$ is hydrogen; lower alkyl; mono- or dichloro-(lower alkyl); mono- or dibromo-(lower alkyl); cycloalkyl of 3 to 7 carbon atoms, unsubstituted or substituted by hydroxy or alkyl of 1 or 2 carbon atoms; cycloalkenyl of 3 to 7 carbon atoms; norbonyl; phenyl, unsubstituted or substituted by 1 to 3 substituents selected from the group consisting of alkyl of 1 or 2 carbon atoms, alkoxy of 1 or 2 carbon atoms, chlorine, bromine, fluorine, trifluoromethyl, nitro, amino, alkyl-sulphenyl of 1 or 2 carbon atoms, and methylenedioxy; azidophenyl; azidoalkyl of 1 to 4 carbon atoms; amino; or thienyl;

$R_4$ is alkylamino of 1 or 2 carbon atoms, or phenylamino; and

E is phenyl or hydroxyphenyl.

As used in this specification -APS- is the group:

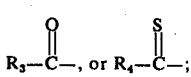

According to another embodiment of the present invention:

A is $R_2$;

B is a direct bond; and

E is phenyl;

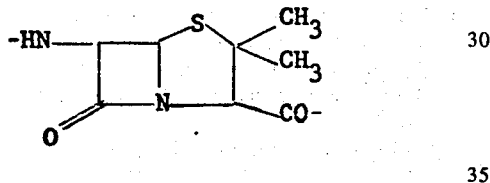 (A)

$R_1$ is hydrogen, nitro or halogen; and $R_2$ is hydrogen, lower alkyl or phenylsulphenyl.

According to another embodiment of the present invention:

A is

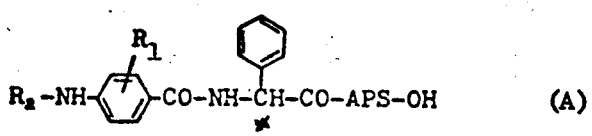

B is a direct bond; and

E is phenyl;

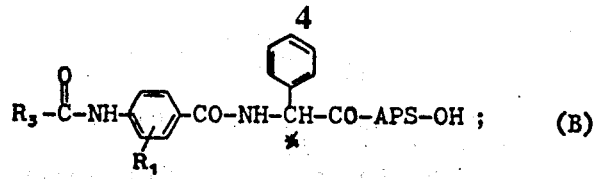 (B)

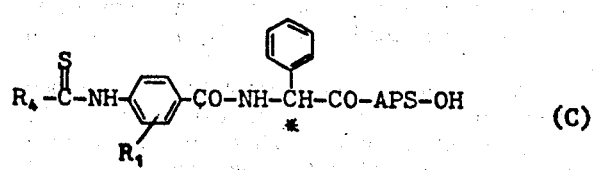 (C)

$R_1$ is hydrogen, nitro or halogen;

$R_3$ is hydrogen; lower alkyl; mono- or dichloro-(lower alkyl); mono- or dibromo-(lower alkyl); cycloalkyl of 3 to 7 carbon atoms, unsubstituted or substituted by hydroxy or alkyl of 1 or 2 carbon atoms; cycloalkenyl of 3 to 7 carbon atoms; norbonyl; phenyl, unsubstituted or substituted by 1 to 3 substituents selected from the group consisting of alkyl of 1 or 2 carbon atoms, alkoxy of 1 or 2 carbon atoms, chlorine, bromine, fluorine, trifluoromethyl, nitro, amino, alkylsulphonyl of 1 or 2 carbon atoms, and methylenedioxy; azidophenyl; azidoalkyl of 1 to 4 carbon atoms; amino; or thienyl; and $R_4$ is alkylamino of 1 or 2 carbon atoms, or phenylamino.

According to another embodiment of the present invention:

A is

B is a direct bond; and

E is phenyl:

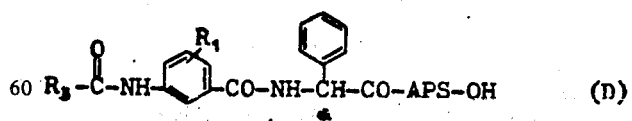 (D)

$R_1$ is hydrogen or halogen; and

R₃ is hydrogen; lower alkyl; cycloalkyl of 3 to 11 carbon atoms or cycloalkenyl of 3 to 11 carbon atoms.

B is CH₂; S—CH₂; CH=CH; or CO—NH—CH₂; and
E is phenyl:

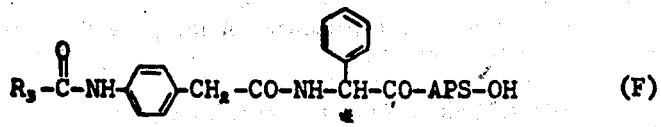 (F)

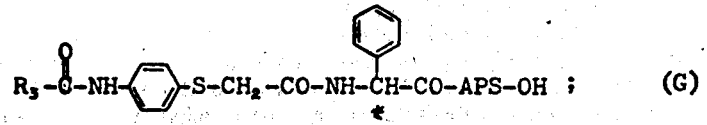 (G)

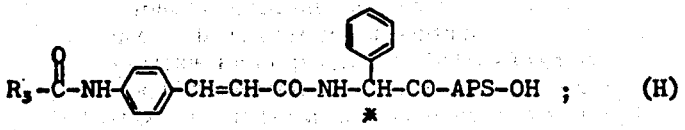 (H)

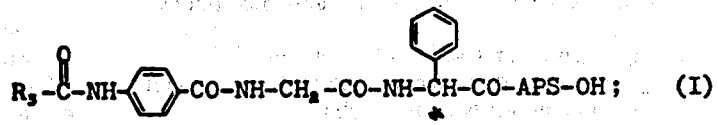 (I)

According to another embodiment of the present invention:
A is

B is a direct bond; and
E is phenyl:

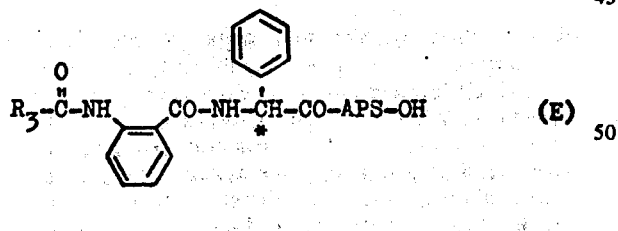 (E)

R₃ is hydrogen; lower alkyl; cycloalkyl of 3 to 11 carbon atoms or cycloalkenyl of 3 to 11 carbon atoms.

According to another embodiment of the present invention:
A is

R₃ is hydrogen; lower alkyl; cycloalkyl of 3 to 11 carbon atoms or cycloalkenyl of 3 to 11 carbon atoms.

According to another embodiment of the present invention:
R₁ is A—NH
A is

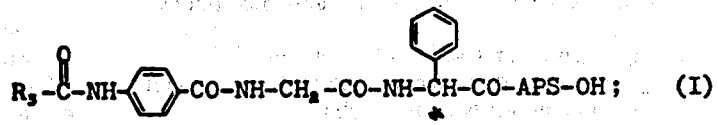

B is a direct bond; and
E is phenyl;

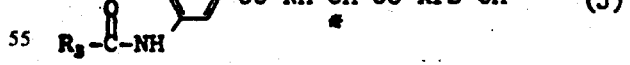 (J)

 (K)

R₃ is hydrogen; lower alkyl; cycloalkyl of 3 to 11 carbon atoms or cycloalkenyl of 3 to 11 carbon atoms.

According to another embodiment of the present invention in compound (A):
C* is in the D(−)- configuraton;
R₁ is hydrogen, nitro, chlorine or bromine; and
R₂ is hydrogen or alkyl of 1 or 2 carbon atoms.

According to another embodiment of the present invention in compounds (B) and (C):
C* is in the D(−)- configuration;
R₁ is hydrogen, nitro, chlorine or bromine;
R₃ is hydrogen; cycloalkyl of 3 to 7 carbon atoms, unsubstituted or substituted by hydroxy or alkyl of 1 or 2 carbon atoms; cycloalkyl of 3 to 7 carbon atoms; norbonyl; phenyl, unsubstituted or substituted by 1 to 3 substituents selected from the group consisting of alkyl of 1 or 2 carbon atoms, alkoxy of 1 or 2 carbon atoms, chlorine, fluorine, trifluoromethyl, nitro, amino, alkylsulphonyl of 1 or 2 carbon atoms, and methylenedioxy; azidophenyl; azidoalkyl of 1 to 4 carbon atoms; amino or thienyl; and
R₄ is alkylamino of 1 or 2 carbon atoms.

According to another embodiment of the present invention in compounds (D) and (E):
C* is in the D(−)- configuration;
R₁ is hydrogen, chlorine or bromine; and
R₃ is hydrogen; lower alkyl; cycloalkyl of 3 to 7 carbon atoms or cycloalkenyl of 3 to 7 carbon atoms.

According to another emdobiment of the present invention in compounds (F), (G), (H) and (I):
C* is in the D(−)- configuration; and
R₃ is hydrogen; lower alkyl; cycloalkyl of 3 to 7 carbon atoms or cycloalkenyl of 3 to 7 carbon atoms.

According to another emdobiment of the present invention in compound (J):
C* is in the D(−)- configuration; and
R₃ is hydrogen; lower alkyl; cycloalkyl of 3 to 7 carbon atoms or cycloalkenyl of 3 to 7 carbon atoms.

According to another embodiment of the present invention in compound (K):
C* is in the D(−)- configuration; and
R₃ is hydrogen; lower alkyl; cycloalkyl of 3 to 7 carbon atoms or cycloalkenyl of 3 to 7 carbon atoms.

According to another embodiment of the present invention:
C* is in the D(−)- configuration;
R₁ is hydrogen;
A is R₂ or

wherein
R₂ is hydrogen; and
R₃ is cycloalkyl of 3 to 7 carbon atoms, cycloalkenyl of 3 to 7 carbon atoms, phenyl or phenyl substituted by amino or 1 to 3 methoxy moieties;
B is a direct bond; and
E is phenyl.

According to another embodiment of the present invention:
R₃ is cyclopropyl, cyclobutyl, cyclopentyl, cycloheptyl, cycloheptenyl, or phenyl substituted by amino or three methoxy moieties.

According to another embodiment of the present invention:
C* is in the D(−)- configuration;
R₁ is hydrogen, nitro, alkyl of 1 or 2 carbon atoms, chlorine, bromine or hydroxy;
A is R₂,

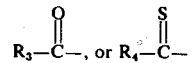

wherein
R₂ is hydrogen or alkyl of 1 or 2 carbon atoms;
R₃ is hydrogen; cycloalkyl of 3 to 7 carbon atoms, unsubstituted or substituted by hydroxy or alkyl of 1 or 2 carbon atoms; cycloalkenyl of 3 to 7 carbon atoms; norbonyl; phenyl unsubstituted or substituted by 1 to 3 substituents selected from the group consisting of alkyl of 1 or 2 carbon atoms, alkoxy of 1 or 2 carbon atoms, chlorine, bromine, fluorine, trifluoromethyl, nitro, amino, alkylsulphonyl of 1 or 2 carbon atoms and methylenedioxy, azidophenyl, adixoalkyl of 1 to 4 carbon atoms; amino; or thienyl;
R₄ is alkylamino of 1 or 2 carbon atoms;
B is a direct bond; CH₂; S—CH₂; or CO—NH—CH₂; and
E is phenyl or hydroxyphenyl.

According to another embodiment of the present invention:
C* is in the D(−)- configuration;
A is

wherein
R₃ is hydrogen; cyclopropyl or cyclobutyl;
B is a direct bond; and
E is phenyl.

According to another embodiment of the present invention:
R₁ is hydrogen, hydroxy, methyl chlorine or nitro; and
R₃ is cyclopropyl, hydroxycyclopropyl, cyclobutyl, cyclopentyl, cyclohexyl, cycloheptyl, cyclopentenyl, ethylcyclopentenyl, cyclohexenyl, cycloheptenyl, methylnorbonyl, phenyl substituted by methoxy, vinyl, fluorine, trifluoromethyl, methylenedioxy, azido, nitro, amino, methylsulphonyl, dimethoxy, dinitro, dichloro, dimethyl, fluorine and amino, or trimethoxy, azidomethyl, azidoethyl, azidodimethylethyl, azidopropyl, ethoxy, methylamino or thienyl, or the sodium salt thereof.

The penicillins and their pharmaceutically acceptable nontoxic salts of the present invention may be produced by reacting an ampicillin derivative of the formula:

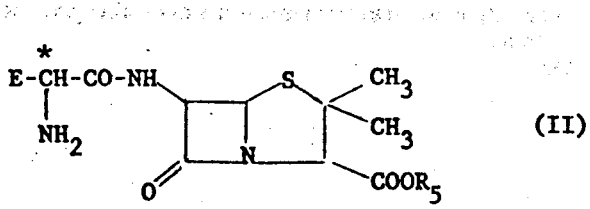

wherein
E is as above defined; and
R₅ is hydrogen, trimethylammonium or a sodium cation with a compound of the formula:

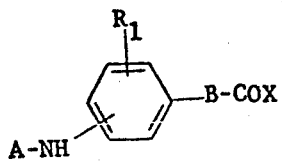

(III)

wherein
R₁, A and B are as above defined; and
X is a labile moiety,
at a temperature of from −20°C to +50°C in a diluent and in the presence of a base.

The labile moiety X can be any moiety that is smoothly eliminated as HX together with a hydrogen atom of the free amino group of the ampicillin derivative of the formula (II) to produce the desired peptide bond. Many such moieties X are known for this purpose from peptide chemistry, the most important for the purposes of the present invention being the halogens (especially chlorine), acyloxy groups (especially acetyl) and activated ester groups (especially benzotriazol-ethoxycarbonyloxy-1-yl).

The synthesis of the activated acylated aromatic amino acid of formula (III) can be carried out by any suitable method; several such methods are known in peptide chemistry, the principal examples for present purposes being the acid chloride method, the mixed anhydride method, and the activated ester method. In the acylated aromatic amino acid of formula (III) (X=OH) is reacted at the carboxyl group in an anhydrous organic solvent and in the presence of about 1 mole equivalent of a tertiary organic base, preferably N-methyl-morpholine, at −60°C to +30°C, preferably −20°C to +10°C; the activated acylated aromatic amino carboxylic acid (III) (X=labile radical) is preferably not isolated, but reacted immediately with a solution of the ampicillin derivative of formula (II). [See T. Wieland & H. Bernhard, Liebig's Ann. Chem. 572, 190 (1951); R. A. Boissonas, Helv. Chem. Acta. 34, 814 (1951); J. R. Vaughan & R. L. Osato, J. Amer. Chem. Soc. 73, 3,547 (1952)].

In the acid chloride method, the acylated aromatic amino acid (III) (X=OH) is generally reacted with thionyl chloride or phosphorus pentachloride in an anhydrous inert organic solvent (e.g. methylene chloride, benzene, tetrahydrofuran (T.H.F.), acetone, dioxane and chloroform) to produce, as the activated acylated aromatic amino acid (III) (X=Cl) the acid chloride.

In the mixed anhydrides method the acylated aromatic amino acid of formula (III) (X=OH) is converted into a mixed anhydride with another carboxylic acid; the residue (X) of the other carboxyl acid is smoothly eliminated in the subsequent reaction with the ampicillin derivative of formula (II). In the most useful form of this method, the acylated aromatic amino acid (III) (X=OH) is reacted with an alkyl acid chlorocarbonate (preferably ethyl chlorocarbonate) in an inert solvent (e.g. tetrahydrofuran); the acid is preferably first converted to its triethylamine salt. The product is an activated acylated aromatic amino carboxylic acid (III) in which X is an acyloxy group (when ethylchlorocarbonate is used,

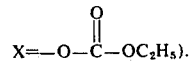

In the activated ester method the acylated aromatic amino acid of formula (III) (X=OH) is converted into an ester by reaction with an alcohol, the residue (X) of which is smoothly eliminated in the subsequent reaction with the ampicillin derivative (II). The most useful activated esters are the 1-hydroxy-benzotriazole esters (W. Konig & R. Geiger, Chem. Ber. 103, 788–798 [1970]), but other activated esters (e.g. the p-nitrophenyl, thiophenyl, cyanomethyl N-ethyl-5-phenyl-isoxazolium-3'-sulphonate, and N-hydroxyphthalimide esters) can be used. The conditions under which the activated esters are formed are those described above.

If 4-cyclopropanecarbonylamino-benzoyl chloride (IVa) and D(−)-α-amino-benzylpenicillin (= ampicillin) (V) are used as starting compounds, the course of the reaction in the process of the invention can be illustrated by the following equation:

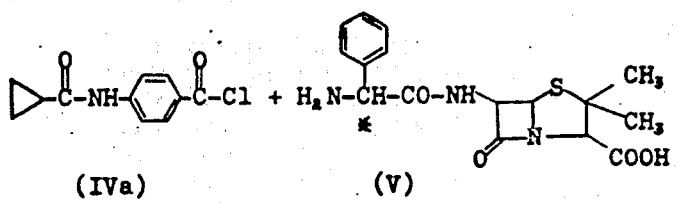

(IVa)     (V)

pH 7.5 | NaOH

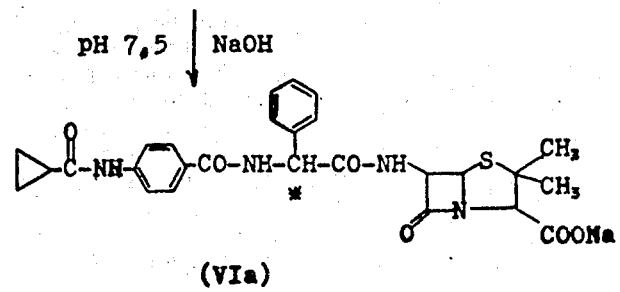

(VIa)

Sodium D(−)-α-(4-cyclopropanecarbonyl-amino-benzoylamino)-benzylpenicillin (VIa) is obtained.

If 4-(4-cycloheptene-1-carbonylamino)-benzoic acid (IVb) and D(−)-α-aminobenzylpenicillin (= ampicillin) (V) are used as starting compounds for a mixed anhydride synthesis, the course of the reaction can be represented by the following equation:

used as starting compounds according to the present invention are in some cases known. The production of typical starting compounds which are not previously known is described in the examples, and the remainder can be produced analogously. The following compounds are representative of the starting materials of the formula (III):

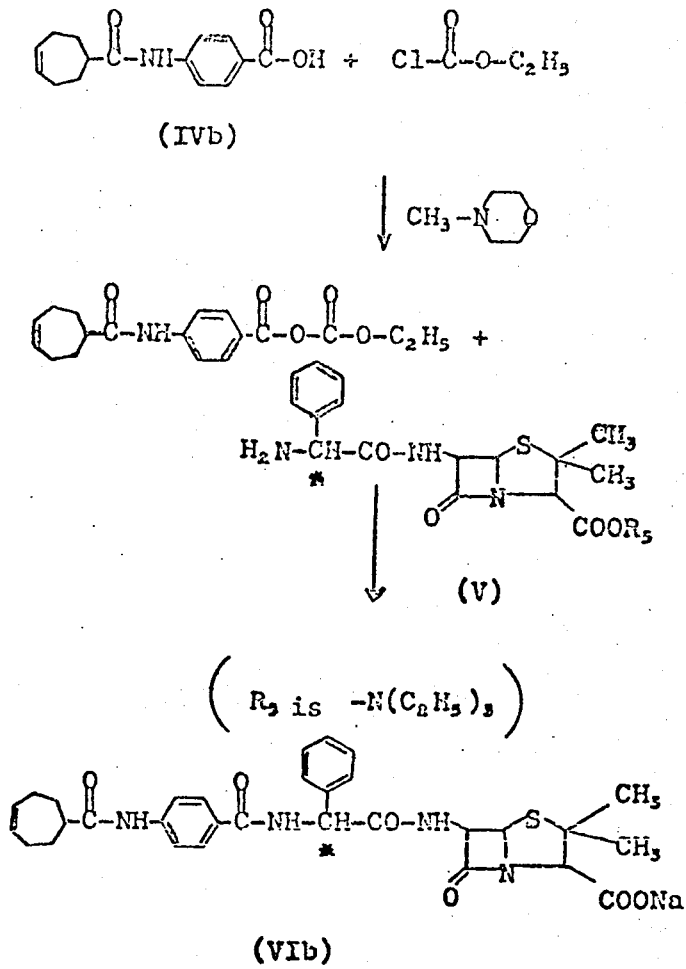

Sodium D(−)-α-[4-(4-cycloheptene-1-carbonylaminobenzoylamino)]-benzylpenicillin (VIb) is obtained.

The compounds of formula (II) used as starting materials according to the present invention are described in German Pat. No. 1,156,078, in U.S. Pat. Nos. 3,342,677, 3,157,600, 2,985,648 and 3,140,282, in South African Pat. No. 68/0290 and in U.S. Pat. No. 3,144,445. They can occur in the D(−)- and L(+)-forms depending on the configuration of the asymmetric carbon atom (C*).

All crystal forms and configurations of the compounds of the formula (II) are suitable as the starting material for the reaction according to the present invention. The configuration of the center of asymmetry of the 6-aminopenicillanic acid nucleus in the compound of the formula (II) should be identical with the corresponding center of asymmetry of 6-aminopenicillanic acid which has been obtained, for example, from penicillin G by fermentative processes.

The compounds of the formula (III) which can be

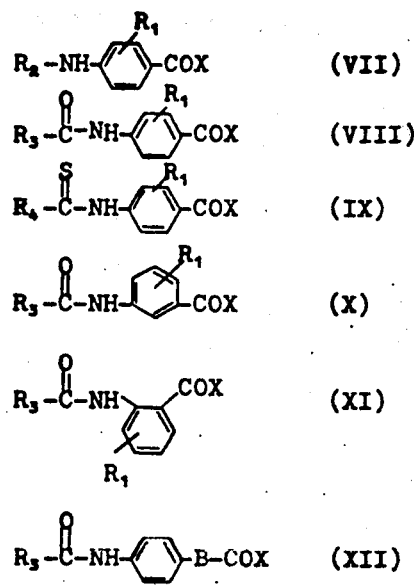

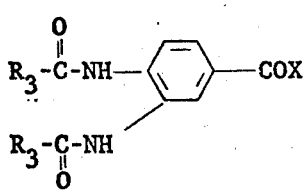

(XIII)

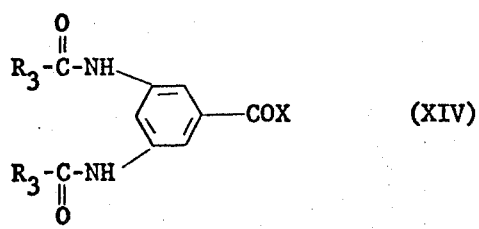

(XIV)

wherein $R_1$, $R_2$, $R_3$, B and X are as above defined.

Possible diluents for the reaction of compounds (II) and (III) are organic solvents, such as acetone, tetrahydrofuran (THF), dioxane, acetonitrile, dimethylformamide (DMF), dimethylsulphoxide and methylene chloride or mixtures of these solvents with water.

The bases used in the reaction of compounds (II) and (III) are generally tertiary organic bases, for example N-methyl-morpholine and triethylamine, or inorganic bases. The pH value of the reaction mixture is kept at pH 6.5 to 9.2 with the aid of these bases. Where a pH measurement is not carried out, as in the case of the mixed anhydride technique using absolute organic solvents (THF/DMF/CH$_2$Cl$_2$), 1.5 to 2.6 mol equivalents of base are preferably added when 6-D-($\alpha$-aminophenylacetamido)-penicillanic acid (ampicillin) and an anhydrous reaction medium are used.

The reaction temperatures can be varied over a substantial range. In general, the reaction is carried out between −20°C and +50°C, temperatures of −15°C to +20°C being particularly preferred.

In carrying out the process according to the present invention, the reactants of formulae (II) and (III) react with one another in equimolecular amounts. It can, however, be desirable to have one of the two reactants present in excess in order to facilitate the isolation of the desired penicillin and to increase the yields. For example, the reactants of the formula (II) can be employed in an excess of 10 to 30% per mol, especially when the mixed anhydride, or activated ester method is used to produce the compound of formula (III). The excess of the reactant of the formula (II) can easily be removed because of its good solubility in aqueous mineral acids when working up the reaction mixture. On the other hand, it is also possible advantageously to employ the reactants of the formula (III) in an excess of, for example, 10% to 20 mol %, especially when the acid chloride method is used to produce the compound of formula (III). This results in the reactants, for example of the formula (II), being utilized better and compensates for the decomposition of the reactants of the formulae (VII) to (XIV) which takes place as a side-reaction in aqueous solvents.

Salts of the present invention can be obtained by reacting the free acid produced with a suitable base.

The following compounds are representative of those of the present invention:

A—NH—⟨⟩—CO—NH—CH—CO—APS—OH
         |$R_1$      |
                     * with $R_1$ and phenyl group

Sodium D(−)-α-(4-cyclopropanecarbonylaminobenzoylamino)-benzylpenicillin:

⟨⟩—CH—CO—APS—ONa
   |
   NH—CO—⟨⟩—NH—CO—◁

(Example 1)

Sodium D(−)-α-(4-cyclobutanecarbonylamino-benzoylamino)-benzylpenicillin:

⟨⟩—CH—CO—APS—ONa
   |
   NH—CO—⟨⟩—NH—CO—◇

(Example 5)

Sodium D(−)-α-(4-cyclopentanecarbonylaminobenzoylamino)-benzylpenicillin:

⟨⟩—CH—CO—APS—ONa
   |
   NH—CO—⟨⟩—NH—CO—⬠

(Example 7)

Sodium D(−)-α-(4-cycloheptanecarbonylaminobenzoylamino)-benzylpenicillin:

15

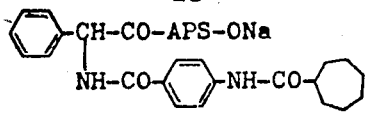

(Example 13)

Sodium D(−)-α-(4-[4-cycloheptene-1-carbonylaminobenzoylamino])-benzylpenicillin:

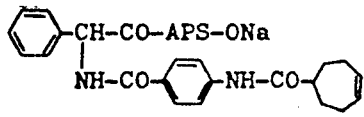

(Example 14)

Sodium D(−)-α-(4-[3,4,5-trimethoxybenzoylaminobenzoylamino])-benzylpenicillin:

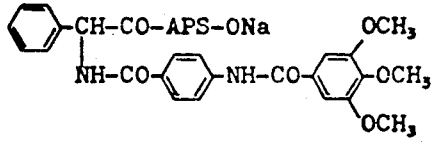

(Example 22)

Sodium D(−)-α-(4-[4-aminobenzoylamino-benzoylamino])-benzylpenicillin:

16

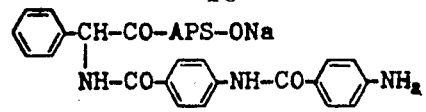

(Example 29)

Sodium D(−)-α-(4-formylamino-benzoylamino)-benzylpenicillin:

(Example 41)

Table 1 which follows shows the in vitro minimum inhibitory concentrations (MIC) in U/ml of nutrient medium. The determination was carried out in a liquid medium in the test tube series dilution test, the reading being taken after 24 hours' incubation at 37°C.

The MIC is determined by the non-turbid test tube in the dilution series. A complete medium of the following composition was used as the growth medium:

| | |
|---|---|
| Lab Lemco (oxoid) | 10 g |
| Peptone (Difco) | 10 g |
| NaCl | 3 g |
| D(+) Dextrose (Merck) | 10 g |
| Buffer pH 7.4 | 1,000 ml |

The penicillin unit (U) referred to in this specification is the standard penicillin unit; 1 mol of penicillin is equivalent to $5.9514 \times 10^8$ U.

Table 1:

| Compound of Example No. | MIC in U/ml Bacterial strain | | | | | | | |
|---|---|---|---|---|---|---|---|---|
| | E. coli | | | | Proteus morg. | | Psdm. aerug. | |
| | 14 | A 261 | C 165 | 183/58 | 932 | 1017 | F 41 | Walter |
| Ampicillin | >1 | | 8 | 200 | 256 | 256 | | >256 |
| 1 | 4 | >256 | 16 | 16 | 8 | ≲32 | 32 | 16 |
| 2 | 4<16 | >256 | 16<64 | 16<64 | >256 | 64<256 | 16<64 | >256 |
| 3 | 4<16 | >256 | 16<64 | 16<64 | 64<256 | 16<64 | 16<64 | 16<64 |
| 4 | 4<16 | >256 | 16<64 | 16<64 | >256 | 64<256 | 64<256 | 64<256 |
| 5 | 8 | >256 | 16 | 32 | 256 | 32 | 64 | 64 |
| 6 | 4<16 | >256 | 16<64 | 4<16 | 64<256 | — | 16<64 | 16<64 |
| 7 | <1 | >256 | 8 | 8 | 256 | 32 | 32 | 32 |
| 8 | 1<4 | >256 | 8 | 16 | 128 | 64 | 64 | 64 |
| 9 | 1<4 | >256 | 16<64 | 4<16 | 64<256 | — | 16<64 | 16<64 |
| 10 | <1 | >256 | 4<16 | 1<4 | 64<256 | 16<64 | 16<64 | 4<16 |
| 11 | 4 | >256 | 8 | 8 | 128 | 64 | 32 | 32 |
| 12 | ~4 | >256 | 8 | 16 | >256 | 16 | 32 | 32 |
| 13 | <1 | 64<256 | 4<16 | 1<4 | 64<256 | 4<16 | 16<64 | 16<64 |
| 14 | <1 | >256 | ~8 | 16 | 256 | 16 | 32 | 32 |
| 15 | 1<4 | >256 | 4<16 | 4<16 | 64<256 | — | 16<64 | 16<64 |
| 16 | ~1 | >256 | 8 | 8 | 256 | 64 | 16 | 16 |
| 17 | 4 | >256 | ~8 | 8 | 128 | ~32 | 32 | 32 |
| 18 | 4 | >256 | 8 | 8 | 128 | 64 | 16 | 16 |
| 19 | <1 | >256 | 4<16 | 4<16 | 64<256 | ~16 | 16<64 | 4<16 |
| 20 | <1 | ~256 | 1<4 | 1<4 | 16<64 | ~4 | 4<16 | ~4 |
| 21 | <1 | ~256 | 4<10 | ~1 | 16<64 | 4<16 | ~16 | 4<16 |
| 22 | 1<4 | >256 | 4<16 | 4<16 | 64<256 | ~16 | 16<64 | 4<16 |
| 23 | <1 | 64<256 | 1<4 | <1 | 16<32 | 1<4 | 4<16 | 4<16 |
| 24 | 1<4 | >256 | 4<16 | 1<4 | 16<64 | 16<64 | 4<16 | 4<16 |
| 25 | 8 | >256 | 16 | 8 | 16 | 128 | 16 | 32 |
| 26 | <1 | 256 | 4 | <1 | 8 | 16 | 16 | 16 |
| 27 | 1<4 | >256 | 16<64 | 4<16 | 64<256 | — | 16<64 | 16<64 |
| 28 | <1 | >256 | 4 | 4 | 128 | 16 | 16 | 16 |
| 29 | <1 | >256 | 4 | 16 | >256 | 256 | ~32 | 32 |
| 30 | ~32 | >256 | 32 | 256 | >256 | >256 | 128 | >256 |
| 31 | 4<16 | >256 | 16<64 | 4<16 | 64<256 | — | 16<64 | 64<256 |
| 32 | 4<16 | >256 | 16<64 | 16<64 | 64<256 | — | 16<64 | 64<256 |

Table 1:-continued

MIC in U/ml
Bacterial strain

| | | | | | | | | |
|---|---|---|---|---|---|---|---|---|
| 33 | ~8 | >256 | ~32 | 32 | 256 | 64 | 64 | 128 |
| 34 | ~16 | >256 | 32 | 128 | >256 | 128 | 64 | 256 |
| 35 | <1 | >256 | 4 | <1 | 128 | ~1 | 4 | 4 |
| 36 | 8 | >256 | ~16 | 32 | 128 | 128 | 32 | ~64 |
| 37 | 4 | >256 | 8 | 16 | ~128 | 128 | ~32 | 32 |
| 38 | 4 | >256 | 16 | 16 | ~256 | 32 | 32 | 32 |
| 39 | 4<16 | >256 | 16<64 | 4<16 | 64<256 | — | 16<64 | 16<64 |
| 40 | 1<4 | >256 | 4<16 | 4<16 | 64<256 | 64<256 | 16<64 | 16<64 |
| 41 | 8 | >256 | 32 | 64 | 128 | 64 | 32 | 64 |
| 42 | 4<16 | >256 | 16<64 | 64<256 | >256 | >256 | 64<256 | 64<256 |
| 43 | ~16 | >256 | 16<64 | 64<256 | >256 | 64<256 | 64<256 | >256 |
| 44 | ~8 | >256 | 16 | 128 | >256 | >256 | ~64 | 256 |
| 45 | <1 | >256 | 8 | 4 | 128 | 16 | 8 | 16 |
| 46 | <1 | 64<256 | ~4 | 1<4 | 64<256 | 16<64 | 4<16 | 4<16 |
| 47 | 16 | >256 | 32 | 128 | >256 | 32 | 64 | >256 |
| 48 | 1<4 | 64<256 | 4<16 | 4<16 | 64<256 | 64<256 | 16<64 | 16<64 |
| 49 | 16<64 | >256 | 64<256 | 64<256 | >256 | 64<256 | <256 | >256 |
| 50 | 16<64 | >256 | 64<256 | 64<256 | >256 | — | >256 | >256 |
| 51 | ~16 | >256 | 16<64 | 16<64 | >256 | — | 64<256 | 64<256 |
| 52 | 32-64 | >256 | 128-256 | 32-64 | >256 | >256 | 128-256 | 128-256 |
| 53 | 32 | >256 | 128-256 | 128-256 | >256 | >256 | 128-256 | >256 |
| 54 | 4<16 | >256 | 16<64 | 4<16 | 64<256 | — | 16<64 | 16<64 |
| 55 | 16>4 | >256 | 64>16 | 64>16 | >256 | >256 | 64>16 | 256>64 |
| 56 | 1<4 | >256 | 4<16 | 4<16 | 64<256 | 16<64 | 4<16 | 4<16 |
| 57 | ~1 | >256 | 4<16 | 1<4 | 64<256 | 64<256 | 4<16 | 4<16 |
| 58 | ~16 | >256 | 64<256 | 16<64 | >256 | >256 | 64<256 | 64<256 |
| 59 | ~4 | >256 | 4<16 | 16<64 | >256 | 4<16 | >256 | >256 |
| 60 | 1<4 | >256 | 4<16 | 16<64 | 64<256 | ~4 | ~256 | 64<256 |
| 61 | 1<4 | >256 | 4<16 | 16<64 | >256 | 64<256 | 64<256 | >256 |
| 62 | 4<16 | >256 | 16<64 | 16<64 | 4<16 | 4<16 | 64<256 | 16<64 |
| 63 | ~1 | >256 | 16<64 | 64<256 | >256 | 64<256 | 64<256 | 64<256 |
| 64 | 1<4 | >256 | 32 | 64 | >256 | 64 | 256 | 128 |
| 65 | 1<4 | >256 | 16<64 | 16<64 | >256 | — | 64<256 | 64<256 |
| 66 | 8 | >256 | 32 | 64 | >256 | 32 | 64 | 128 |
| 67 | 1<4 | >256 | 16<64 | 4<16 | >256 | >256 | 64<256 | 64<256 |
| 68 | 1<4 | >256 | 16<64 | 4<16 | 64<256 | — | 64<256 | 64<256 |
| 69 | 1<4 | >256 | 16<64 | 16<64 | 64<256 | — | 64<256 | 64<256 |
| 70 | 4<16 | >256 | 16<64 | 64<256 | >256 | — | 64<256 | >256 |
| 71 | ~4 | >256 | 4<16 | 64<256 | >256 | 64<256 | 16<64 | 64<256 |
| 72 | 1<4 | >256 | 4<16 | 4<16 | >256 | 64<256 | 64<256 | 64<256 |
| 73 | 4<16 | >256 | 16<64 | 4<16 | 64<256 | — | 64<256 | 64<256 |
| 74 | 4<16 | >256 | 16<64 | 64<256 | >256 | — | 64<256 | >256 |
| 75 | 4<16 | >256 | 16<64 | 16<64 | >256 | — | 16<64 | 64<256 |
| 76 | <4 | >256 | 16<64 | 16<64 | >256 | 64<256 | >256 | >256 |

| Compound of Example No. | Klebsiella | | Staph. aureus | | ENTEROCOCCUS 9790 ATCC |
|---|---|---|---|---|---|
| | K 10 | 63 | 756 | 33 | |
| Ampicillin | | | 128 | 256 | <1 | 4 |
| 1 | 64 | 64 | 64 | <1 | ~8 |
| 2 | 64<256 | 64<256 | 16<64 | <1 | 4<16 |
| 3 | 64<256 | 16<64 | 16<64 | 1<4 | 4<16 |
| 4 | 64<256 | 64<256 | 16<64 | <1 | 4<16 |
| 5 | 128 | 64 | 32 | <1 | 16 |
| 6 | 16<64 | 16<64 | 16<64 | <1 | 16<64 |
| 7 | 32 | 32 | 64 | <1 | 8 |
| 8 | 64 | 32 | 8 | <1 | 8 |
| 9 | 16<64 | 16<64 | 64<256 | <1 | 4<16 |
| 10 | 16<64 | 16<64 | 4<16 | <1 | ~16 |
| 11 | 64 | 32 | 128 | <1 | 16 |
| 12 | 32 | 32 | 16 | <1 | ~8 |
| 13 | 16<64 | 4<16 | 4<16 | <1 | 4<16 |
| 14 | 32 | 32 | 32 | <1 | 8 |
| 15 | 16<64 | 16<64 | 16<64 | <1 | 4<16 |
| 16 | 32 | 16 | 64 | <1 | 8 |
| 17 | 64 | 32 | 32 | <1 | 16 |
| 18 | 64 | 64 | 16 | <1 | 8 |
| 19 | 16<64 | 16<64 | 1<4 | <1 | 4<16 |
| 20 | 4<16 | 4<16 | ~4 | <1 | ~4 |
| 21 | 16<64 | 16<64 | 4<16 | <1 | ~4 |
| 22 | 16<64 | 16<64 | 4<16 | <1 | 1<4 |
| 23 | 4<16 | 4<16 | 1<4 | <1 | 4<16 |
| 24 | 16<64 | 4<16 | 4<16 | <1 | 1<4 |
| 25 | 64 | 32 | 64 | <1 | 8 |
| 26 | 16 | 4 | 64 | <1 | 6 |
| 27 | 16<64 | 16<64 | 16<64 | <1 | 4<16 |
| 28 | 16 | 16 | ~32 | <1 | 4 |
| 29 | 128 | 64 | 32 | <1 | 4 |
| 30 | >256 | 256 | 64 | <1 | 8 |
| 31 | 16<64 | 64<256 | 64<256 | <1 | 4<16 |
| 32 | 64<256 | 16<64 | 16<64 | <1 | 4<16 |
| 33 | 128 | 128 | 32 | <1 | 4 |
| 34 | 256 | 128 | 32 | <1 | ~4 |
| 35 | 16 | 8 | 8 | <1 | ~4 |
| 36 | 128 | 64 | 64 | <1 | 8 |
| 37 | 64 | 32 | 64 | <1 | 16 |
| 38 | 128 | 64 | 32 | <1 | ~16 |

Table 1:-continued

| | MIC in U/ml Bacterial strain | | | | |
|---|---|---|---|---|---|
| 39 | 64<256 | 16<64 | ~64 | <1 | 4<16 |
| 40 | 64<256 | 16<64 | 16<64 | <1 | 4<16 |
| 41 | 128 | 128 | 32 | <1 | 8 |
| 42 | >256 | 64<256 | 4<16 | <1 | ~4 |
| 43 | 64<256 | 64<256 | 64<256 | <1 | 4<16 |
| 44 | 256 | 128 | 64 | <1 | 4 |
| 45 | 32 | 16 | 16 | <1 | <1 |
| 46 | 16<64 | 16<64 | 1<4 | <1 | ~4 |
| 47 | 256 | 128 | 64 | <1 | 4 |
| 48 | 16<64 | 16<64 | 4<16 | <1 | 4<16 |
| 49 | >256 | >256 | 16<64 | <1 | 4<16 |
| 50 | >256 | 64<256 | 16<64 | <1 | 16<64 |
| 51 | 64<256 | 64<256 | 16<64 | <1 | 4<16 |
| 52 | 128–256 | 128–256 | 32–64 | <1 | 32–64 |
| 53 | >256 | 128–256 | 32–64 | <1 | 2–4 |
| 54 | 16<64 | 16<64 | 16<64 | <1 | 16<64 |
| 55 | 256>64 | 256>64 | 64>16 | <1 | 64>16 |
| 56 | 16<64 | 16<64 | 4<16 | <1 | 4<16 |
| 57 | 16<64 | 16<64 | 4<16 | <1 | 4<16 |
| 58 | 64<256 | 64<256 | 4<16 | <1 | 4<16 |
| 59 | 64<256 | 16<64 | 4<16 | <1 | 4<16 |
| 60 | 16<64 | 16<64 | 1<4 | 1<4 | 4<16 |
| 61 | 16<64 | 16<64 | 4<16 | <1 | ~16 |
| 62 | 16<64 | 16<64 | 16<64 | 1<4 | 4<16 |
| 63 | 64<256 | 64<256 | 4<16 | <1 | 4 |
| 64 | 128 | 64 | 16 | 1<4 | 8 |
| 65 | 64<256 | 16<64 | 16<64 | <1 | 4<16 |
| 66 | 64 | 32 | 32 | <1 | 32 |
| 67 | 16<64 | 16<64 | 16<64 | <1 | 4<16 |
| 68 | 16<64 | 16<64 | 16<64 | <1 | 16<64 |
| 69 | 16<64 | 16<64 | 16<64 | <1 | 4<16 |
| 70 | 64<256 | 64<256 | 16<64 | <1 | 16<64 |
| 71 | 64<256 | 64<256 | 16<64 | <1 | 4<16 |
| 72 | 16<64 | 16<64 | 16<64 | <1 | ~16 |
| 73 | 64<256 | 16<64 | 64<256 | <1 | 16<64 |
| 74 | <256 | 64<256 | 16<64 | <1 | 4<16 |
| 75 | 64<256 | 64<256 | 16<64 | <1 | ~16 |
| 76 | 16<64 | 16<64 | 4<16 | <1 | ~16 |

This table shows that the penicillins and their pharmaceutically acceptable nontoxic salts display strong anti-bacterial activity. Their activity extends to both Gram-positive and Gram-negative bacteria, of which the following families of bacteria, genera of bacteria and varieties of bacteria may be mentioned as examples: from the family of the Enterobacteriaceae, for example Escherichia (especially Escherichia coli), Klebsiella (especially *Klebsiella pneumoniae*) and *Enterobacter aerogenes*, Serratia, Proteus (especially *Proteus vulgaris*, *Proteus mirabilis*, *Proteus morganii* and *Proteus rettgeri*) and Salmonella (especially *Salmonella enteritidis*;

from the family of the Micrococcaceae, for example *Staphylococcus aureus* and *Staphylococcus epidermidis*;

from the family of the Lactobacteriaceae, for example *Streptococcus pyogenes* and *Streptococcus faecalis* (Enterococcus).

The penicillins and their pharmaceutically acceptable nontoxic salts have proved especially effective in the therapy of infections caused by Klebsiella, Proteus and Pseudomonas bacteria (see Table 2).

The penicillin of Example 1A was diluted with Muller-Hinton nutrient broth, with addition of 0.1% of glucose, per content of 100 µg/ml. The nutrient solution contained $1 \times 10^5$ to $2 \times 10^5$ bacteria per milliliter in each case. The test tubes containing this mixture were each incubated for 24 hours and thereafter the degree of turbidity was determined. The absence of turbidity showed an effect. At a dosage of 100 µg/ml, the following bacterial cultures were non-turbid: E. coli 14; E. coli c165; *Proteus vulgaris* 1017; Klebsiella K 10; Klebsiella 63; Salmonella sp.; Shigella sp.; Enterobacter sp.; Serratia sp.; Proteus, indole-negative, sp.; Proteus, indole-positive, sp.; *Pasteurella pseudotuberculosis*; Brucella sp.; *Haemophilus influenzae*; *Bordetella bronchiseptica*; Bacteroides sp.; *Staphylococcus aureus* 133; *Neisseria cartarrhalis* sp.; *Diplococcus pneumoniae* sp.; *Streptococcus pyogenes* W; Enterococcus sp.; Lactobacillus sp.; *Corynebacterium diphteriae gravis*; *Corynebacterium pyogenes* M; *Clostridium botulinium*; *Clostridium tetani*; Borrelia sp.; *Pseudomonas aeruginosa* sp.; *Aeromonas hydrophila* sp..

Table 2

| | Data from animal experiment | | | | | | | |
|---|---|---|---|---|---|---|---|---|
| | Surviving animals (%) on: | | | | | | | |
| Bacterium and subcutaneous dose in Units per experiment animal | 1st | 2nd | 3rd | 5th | 1st | 2nd | 3rd | 5th |
| | day after infection | | | | day after infection | | | |
| | Carbenicillin | | | | Compound of invention: | | | |
| Klebsiella 62 | | | | | Compound of Ex.1: | | | |
| 2 × 3000 | 0 | | | | 100 | 100 | 50 | 50 |
| Klebsiella 63 | | | | | Compound of Ex.7: | | | |
| 2 × 3000 | 0 | | | | ·100 | 100 | 20 | — |
| Psdm. aerug. | | | | | Compound of Ex.22: | | | |
| F 41 | 50 | 0 | | | 80 | 80 | 80 | — |
| 4 × 3000 | | | | | | | | |
| Psdm. aerug. | | | | | Compound of Ex.29: | | | |
| F 41 4 × 3000 | 80 | 30 | 30 | 20 | 100 | 80 | 70 | 70 |
| Klebsiella 63 | | | | | Compound of Ex.41: | | | |

Table 2-continued

| Bacterium and subcutaneous dose in Units per experiment animal | Data from animal experiment Surviving animals (%) on: | | | | | | | |
|---|---|---|---|---|---|---|---|---|
| | 1st | 2nd | 3rd | 5th | 1st | 2nd | 3rd | 5th |
| | day after infection | | | | day after infection | | | |
| | Carbenicillin | | | | Compound of invention: | | | |
| 2 × 3000 | 0 | | | | 80 | 50 | 50 | 50 |

Test animal: white mouse (Winkelmann)
Infection: intraperitoneal

The pharmaceutical compositions of the present invention contain a major or minor amount, e.g. 99.5% to 0.1%, preferably 95% to 0.5%, of at least one penicillin as above defined in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 25,000 to 1,000,000 U/kg of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose for oral and parenteral administration is $1.25 \times 10^6$ to $90 \times 10^6$U of active ingredient.

The penicillins and their pharmaceutically acceptable nontoxic salts are useful not only for their broad antibacterial activity but also may be used for preventing systemic and topical bacterial infections and for treating such infections after they have occurred.

The present invention also comprises an animal feedstuff which comprises a nutritious material in combination with an anti-bacterially effective amount of a compound of the present invention. The present invention also includes the mixture of a compound of the present invention with animal fodder or drinking water in order to promote the growth of the animal.

The penicillins and their pharmaceutically acceptable nontoxic salts can also be combined with other substances in order to enhance the anti-bacterial effect. For example, isoxazolyl-penicillins may be combined with those of the present invention in order to inhibit the decomposition of the compounds of the present invention.

The following non-limitative examples more particularly illustrate the present invention:

The β-lactam content of the penicillins was determined iodometrically and in some cases by means of IR spectroscopy.

All N-acylated aromatic amino acids of the structural formulae (VII) to (XIV) were examined by thin layer chromatography on DC plates with silica gel F-254 (Messrs. Merck, Darmstadt).

The following served as migrating agents:

| | | |
|---|---|---|
| SBA: | 75 | % by volume of sec.-butanol |
| | 13.5 | % by volume of 90 per cent strength formic acid |
| | 11.5 | % by volume of water |
| SBN: | 85 | % by volume of sec.-butanol |
| | 15 | % by volume of 10 per cent strength ammonia |
| PEW: | n-propanol/ethyl acetate water (4:3:3) | |
| CMA: | 95 | % by volume of chloroform |
| | 5 | % by volume of methanol |
| | 3 | % by volume of glacial acetic acid. |

Compounds with a free amino group were rendered visible by spraying with a 5 per cent strength solution of ninhydrin in a mixture of n-butanol and 2 N acetic acid (95:5, V/V) and brief heating in a drying cabinet (80°-100°C). More frequently, however, the chlorine-tolidine reaction — spraying with tert.-butyl hypochlorite and subsequently (after brief heating) with a solution of o-tolidine and potassium chloride containing acetic acid — was used. [Literature: R. H. Mazur, B. W. Ellis and P. S. Cannaratu, J. biol. Chemistry 237, 1619 (1962) and E. von Arx and R. Neher, J. Chromatogr. (Amsterdam) 12, 329 (1963)].

All intermediate compounds and penicillins described in the present invention show an IR spectrum corresponding to their structure.

All the penicillins were subjected to an analytical counter-current distribution over the course of 29 hours, using petroleum ether/ethyl acetate/dimethylformamide/water (3:7:5:5) as the distribution system.

The NMR spectra of penicillins were recorded in $CD_3OD$ solution.

In calculating the elementary analyses, the water content of the penicillins has been taken into account.

The figures (U/ml) quoted for the reactivities against bacterial strains are minimum inhibitory concentrations in the test tube series dilution test after 24 hours' incubation.

EXAMPLE 1

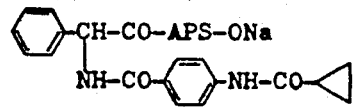

A. 10 g (0.027 mol) of sodium D(−)-α-aminobenzylpenicillin [= sodium ampicillin or sodium 6-(α-aminophenylacetylamino)-penicillanate] were dissolved in 100 ml of THF with addition of 20 ml of water. After cooling the reaction mixture to between 0° and 5°C, 7.5 g (0.0336 mol) of 4-cyclopropanecarbonylamino-benzoyl chloride dissolved in 40 ml of THF were added dropwise over the course of 30 minutes while cooling with ice/water and keeping the pH value at between 7.5 and 7.8 by simultaneous addition of 2 N sodium hydroxide solution. The mixture was stirred for 30 minutes at 0° to 5° and subsequently for 2.5 hours at room temperature, during which time the pH value was kept constant at 7.5 by adding a little 2 N sodium hydroxide solution. After distilling off the THF, a viscous mass remained, which was dissolved in 300 ml of water and extracted once with ethyl acetate.

The aqueous phase was separated off, cooled to 0°, covered with 250 ml of ethyl acetate and acidified with 2 N HCl to a pH value of 2.0. The organic phase was separated off and the aqueous phase was extracted twice more with 80 ml of ethyl acetate. The combined ethyl acetate extracts were washed with water until neutral and dried over $Na_2SO_4$ in a refrigerator. After evaporating off the solvent, a light resinous product remained, which was taken up in 80 ml of absolute methanol and treated with an equivalent proportion of a molar solution of sodium 2-ethyl-hexanoate in ether containing methanol. The solution was gently concentrated to dryness in vacuo and the residue was recrystallized from 90 ml of absolute methanol and 600 ml of absolute ether.

Yield relative to sodium ampicillin: 9.4 g (62.5%) of sodium D(−)-α-(4-cyclopropanecarbonylamino-benzoylamino)-benzylpenicillin:

β-Lactam content: 91.7%

$C_{27}H_{27}N_4O_6SNa \cdot 1H_2O$ (576.6). Calculated. C, 56.24; H, 4.89; N, 9.72; S, 5.58. Found. C, 55.2; H, 5.4; N, 9.2; S, 6.0.

B. 4-Cyclopropanecarbonylamino-benzoic acid.

20 g (0.146 mol) of p-aminobenzoic acid (PAB) were dissolved in 80 ml of THF and 20.4 ml (0.146 mol) of triethylamine were next added to the solution. Thereafter, 22.5 g (0.216 mol) of cyclopropanecarboxylic acid chloride in 40 ml of THF were rapidly added dropwise while cooling with ice. At the end of the dropwise addition, a further 9.4 ml of triethylamine were introduced all at once into the suspension (pH = 7 to 8). The reaction solution was boiled for 5 hours under reflux and then cooled to room temperature, and thereafter the solvent was distilled off in vacuo. The residue which remained was dissolved in water and the resulting solution was rendered acid with 2 N HCl (pH 2.0). The residue was filtered off, thoroughly washed with water on the filter and finally dried in air. It was recrystallized from THF/petroleum ether.

Yield: 28.0 g (93.6%)

$C_{11}H_{11}NO_3$ (205.2) Calculated. C, 64.39; H, 5.40; N, 6.82. Found. C, 64.9; H, 5.6; N, 6.0.

C. 4-Cyclopropanecarbonylamino-benzoyl chloride.

12 g (0.0585 mol) of 4-cyclopropanecarbonylaminobenzoic acid were suspended in 35 g of analytical grade benzene. The mixture was treated for several hours with 17 g of thionyl chloride and 0.2 ml of DMF at 60°C, until the evolution of gas had ceased. The solution was concentrated to dryness in vacuo, the residue was dissolved in THF and the solvent was distilled off completely.

Yield: 9.5 g (73%)

$C_{11}H_{10}ClNO_2$ (223.7).

Calculated. C, 59.06; H, 4.51; N, 6.26; Cl, 15.85. Found. C, 58.01; H, 4.8; N, 5.5; Cl, 15.5. NMR signals at δ: 1.0 – 1.3 ppm (5 H) 7.6 – 8.2 ppm (4 H)

EXAMPLE 2

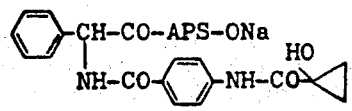

A. Condensation:

The cold solution of the unsymmetrical anhydride, prepared according to B, was treated at −15°C with the solution of the amine component, prepared according to C, which was also cooled. The mixture was stirred overnight with the temperature gradually rising from −15° to +15°. On the following day the solvent was stripped off in vacuo (bath temperature 20°), the residue was stirred with 300 ml of water and the solution thereby produced was extracted once with ethyl acetate. The aqueous phase was cooled to 0°, covered with 200 ml of ethyl acetate and acidified with 2 N HCl. The aqueous solution was extracted twice more with 100 ml of ethyl acetate at a time. The combined organic solvent extracts were thoroughly washed with water and thereafter dried over $Na_2SO_4$ in a refrigerator. After filtration, the solution was concentrated in vacuo, reacted with an equivalent amount of a 1-molar solution of sodium 2-ethyl-hexanoate at ether containing methanol, and the mixture was left to stand for 10 minutes at 0°C. Thereafter the solvent was distilled off and the resulting semi-solid mass was reprecipitated from 90 ml of analytical grade methanol and 600 ml of analytical grade ether, filtered off and dried for 5 hours in a desiccator over $P_2O_5$ by means of a high vacuum.

Yield relative to the carboxyl component B: 8.4 g (70.5%) of sodium D(−)-α-(4-cyclopropanol-1-carbonyl-aminobenzoylamino)-benzylpenicillin:

$C_{27}H_{27}N_4O_7SNa$ . $2H_2O$ (610.6): Calculated: C, 53.11; H, 5.11; N, 9.17; S, 5.26. Found: C, 52.5; H, 5.9; N, 8.3; S, 5.5.

β-Lactam content: 93.8%

NMR signals at δ: 1.1 – 1.4 (4H); 1.5 (6H); 4.1 (1H); 4.2 (1H); 5.5 (2H); 5.9 (1H); 7.3 – 7.4 ppm (9H).

B. Activation of the carboxyl component:

4.6 g (0.0208 mol) of 4-(1-hydroxycyclopropanecarbonylamino)-benzoic acid were dissolved in 20 ml of absolute DMF and 40 ml of absolute THF, 2.35 ml (0.021 mol) of N-methylmorpholine were added followed, after cooling to −15°C, by 2.1 ml (0.0218 mol) of chloroformic acid ethyl ester, and the mixture was stirred for 15 minutes at −15° to −10°C.

C. Preparation of the amine component:

8.7 g (0.025 mol) of D(−)-α-aminobenzylpenicillin (=ampicillin) were suspended in 70 ml of $CH_2Cl_2$ and 5.6 ml (0.04 mol) of triethylamine in the presence of anhydrous $Na_2SO_4$ at −10° and the mixture was then stirred for 1.5 hours at room temperature. Thereafter the solution was freed of the $Na_2SO_4$ by filtration and was stored at −10°C for the next reaction step.

EXAMPLE 3:

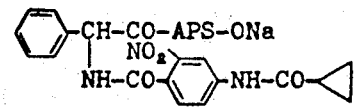

A. This penicillin was synthesized as described in Example 2 by the mixed anhydride method from 29 g (0.0116 mol) of 4-cyclopropanecarbonylamino-2-nitro-benzoic acid, 1.4 ml (0.0125 mol) of N-methylmorpholine and 1.2 ml (0.0125 mol) of chloroformic acid ethyl ester.

4.89 g (0.014 mol) of ampicillin and 3.14 ml (0.0224 mol) of triethylamine were used as the amine component.

Yield: 5.1 g (74%) of sodium D(−)-α-(4-cyclopropanecarbonylamino-2-nitrobenzoylamino)-benzylpenicillin:

$C_{27}H_{26}N_5O_8SNa$ . $2H_2O$ (639.6) Calculated: C, 50.70; H, 4.72; N, 10.95; S, 5.02. Found: C, 51.0; H, 6.1; N, 10.0; S, 5.7.

β-Lactam content: 93.2%

B. 4-Cyclopropanecarbonylamino-2-nitrobenzoic acid 6 g (0.033 mol) of 4-amino-2-nitrobenzoic acid were dissolved in a mixture (100 ml) of THF and water (1:1). The solution was adjusted to pH 8.5 with 2 N NaOH and reacted at room temperature with 3.78 g (0.0363 mol) of cyclopropanecarboxylic acid chloride in 25 ml of THF. The pH value of the reaction solution was kept at 8.0 – 8.5 to the end by further addition of 2 N sodium hydroxide solution. After a reaction time of 3.5 hours, the solvent was next distilled off. The residue was diluted with water and the aqueous solution was extracted by shaking once with ethyl acetate and was finally acidified with 2 N HCl to pH 2.0. The oil which precipitated was isolated by extraction with ethyl acetate. After washing and drying the ethyl acetate phase, the solution was concentrated to dryness. The product was crystallized from ethyl acetate/petroleum ether.

Thin layer chromatography: a single product in PEW, SBA and CMA.

Yield: 3.0 g (36.4%)

$C_{11}H_{10}N_2O_5$ (250.2) Calculated. C, 52.81; H, 4.03; N, 11.20. Found. C, 51.9; H, 4.2; N, 11.4.

EXAMPLE 4

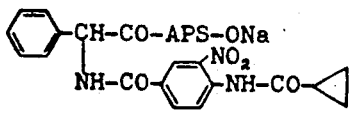

A. This penicillin was prepared as described in Example 2 from 6.32 g (0.0252 mol) of 4-cyclopropanecarbonylamino-3-nitro-benzoic acid, 2.94 ml (0.0262 mol) of N-methylmorpholine, 2.52 ml (0.0262 mol) of chloroformic acid ethyl ester and 10.6 g (0.0302 mol) of ampicillin and 6.85 ml (0.049 mol) of TEA.

Yield: 10.2 g (67%) of sodium D(−)-α-(4-cyclopropanecarbonylamino-3-nitro-benzoylamino)-benzylpenicillin:

$C_{27}H_{26}N_5O_8SNa \cdot 2H_2O$ (639.6) Calculated. C, 50.7; H, 4.72; N, 10.95; S, 5.02. Found. C, 47.8; H, 5.0; N, 10.1; S, 5.3.

β-Lactam content: 84.9%

B. 4-Cyclopropanecarbonylamino-3-nitro-benzoic acid

The acylation of 7.0 g (0.0384 mol) of 3-nitro-4-amino-benzoic acid with 4.42 g (0.0423 mol) of cyclopropanecarboxylic acid chloride was carried out as described in Example 3.

Yield: 6.4 g (66.6%)

$C_{11}H_{10}N_2O_5$ (250.2) Calculated. C, 52.81; H, 4.01; N, 11.20. Found. C, 50.4; H, 4.0; N, 11.7.

EXAMPLE 5

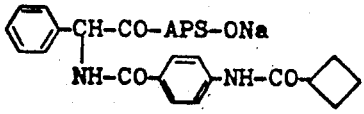

A. The penicillin was produced as described in Example 2 from:

1. 5.29 g (0.0239 mol) of 4-cyclobutanecarbonylamino-benzoic acid, 2.78 ml (0.0248 mol) of N-methylmorpholine and 2.38 ml (0.0248 mol) of chloroformic acid ethyl ester.

2. 10.0 g (0.0286 mol) of ampicillin and 6.47 ml (0.0462 mol) of triethylamine.

Yield: 11.6 g (84.7%) of sodium D(−)-α-(4-cyclobutanecarbonylaminobenzoylamino)-benzylpenicillin:

$C_{28}H_{29}N_4O_6SNa \cdot 2H_2O$ (608.648) Calculated. C, 55.26; H, 5.46; N, 9.20; S, 5.28. Found. C, 54.5; H, 6.4; N, 8.8; S, 5.8.

β-Lactam content: 97.7%.

B. 4-Cyclobutanecarbonylamino-benzoic acid was prepared as described in Example 3 from 7.05 g (0.0514 mol) of p-aminobenzoic acid (PAB) and 6.4 g (0.054 mol) of cyclobutanecarboxylic acid chloride.

Yield: 6.7 g (59.4%)

$C_{12}H_{13}NO_3$ (219.243) Calculated. C, 65.75; H, 5.98; N, 6.39. Found. C, 64.2; H, 6.0; N, 6.1.

EXAMPLE 6

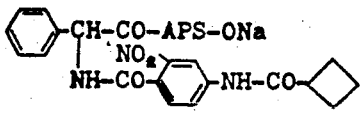

A. The penicillin was prepared as described in Example 2 from:

1. 5.5 g (0.0208 mol) of 4-cyclobutanecarbonylamino-2-nitrobenzoic acid, 2.46 ml (0.022 mol) of N-methylmorpholine and 2.11 ml (0.022 mol) of chloroformic acid ethyl ester.

2. 8.72 g (0.025 mol) of ampicillin and 5.6 ml (0.04 mol) of triethylamine.

Yield: 8.8 g (68.8%) of sodium D(−)-α-(4-cyclobutanecarbonylamino-2-nitro-benzoylamino)-benzylpenicillin:

$C_{28}H_{28}N_5O_8SNa \cdot 2H_2O$ (653.646) Calculated. C, 51.45; H, 4.93; N, 10.71; S, 4.91. Found. C, 52.4; H, 5.8; N, 10.1; S, 5.3.

β-Lactam content: 91.0%.

B. 4-Cyclobutanecarbonylamino-2-nitro-benzoic acid was prepared as described in Example 3 from 10.9 g (0.06 mol) of 4-amino-2-nitro-benzoic acid and 7.83 g (0.066 mol) of cyclobutanecarboxylic acid chloride.

Yield: 6.3 g (the product was recrystallized from ethyl acetate/petroleum ether).

$C_{12}H_{12}N_2O_5$ (264.240) Calculated. C, 54.56; H, 4.58; N, 10.60. Found. C, 54.2; H, 4.9; N, 10.60.

EXAMPLE 7

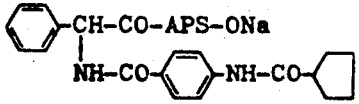

A. 8.1 g (0.0323 mol) of 4-cyclopentane-carbonylaminobenzoyl chloride were reacted with 10.0 g (0.0269 mol) of sodium D(−)-α-aminobenzylpenicillin (sodium ampicillin) as described in Example 1.

Yield: 14 g (88.5%) of sodium D(−)-α-(4-cyclopentanecarbonylamino-benzoylamino)-benzylpenicillin B. 4-Cyclopentanecarbonylamino-benzoic acid was prepared as described in Example 1B from 31.5 g (0.23 mol) of p-aminobenzoic acid and 17.3 g (0.23 mol) of cyclopropanecarboxylic acid chloride in the presence of triethylamine.

Yield: 31.8 g (59.5%); product reprecipitated from THF/petroleum ether.

$C_{13}H_{15}NO_3$ (233.270) Calculated. C, 66.93; H, 6.48; H, 6.00. Found. C, 66.4; H, 6.6; N, 5.8.

C. 4-Cyclopentanecarbonylamino-benzoyl chloride:

25.9 g (0.111 mol) of 4-cyclopentane-carbonylaminobenzoic acid were converted into the acid chloride by means of 12.1 ml (0.166 mol) of thionyl chloride in the presence of $CH_2Cl_2$, while boiling under reflux.

Yield: 26 g (94%)

$C_{13}H_{14}NO_2Cl$ (251.713) Calculated. C, 62.03; H, 5.61; N, 5.57; Cl, 14.08. Found. C, 60.4; H, 5.6; N, 5.6; Cl, 13.3.

EXAMPLE 8

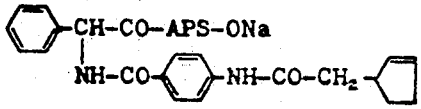

A. The penicillin was prepared as described in Example 2 from:

1. 5.85 g (0.0239 mol) of )α4-(2-cyclopentene-1-acetamido)-benzoic acid, 2.78 ml (0.0248 mol) of N-methylmorpholine and 2.38 ml (0.0248 mol) of chloroformic acid ethyl ester.

2. 10.0 g (0.0286 mol) of ampicillin and 6.47 ml (0.0462 mol) of triethylamine.

Yield: 10.0 g (70%) of sodium D(−)-α-(4-[2-cyclopentene-1-acetamido-benzoylamino])-benzylpenicillin $C_{30}H_{31}N_4O_6SMg \cdot 2H_2O$ (634.7) Calculated. C, 56.78; H, 5.56; N, 8.83; S, 5.06. Found. C, 56.7; H, 5.7; H, 8.1; S, 4.5.

β-Lactam content: 98.2%

B. 4-(2-Cyclopentene-1-acetamido)-benzoic acid was prepared as described in Example 3 from 8.25 g (0.06 mol) of p-aminobenzoic acid and 9.5 g (0.067 mol) of 2-cyclopentene-1-acetyl chloride.

Yield: 13.3 g (90.5%)

Thin layer chromatogram: a single substance in PEW, SBA and MCA (ninhydrin negative)

$C_{14}H_{15}NO_3$ (245.3) Calculated. C, 68.56; H, 6.16; N, 5.71. Found. C, 63.0; H, 5.7; N, 5.3.

NMR signals at δ =7.7 − 8.1 (4H), 5.8 (2H), 2.5 (2H), 2.0 − 2.4 ppm (5H)

EXAMPLE 9

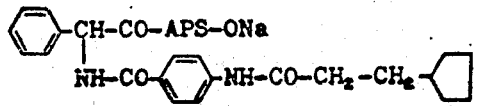

A. The penicillin was prepared as described in Example 2 from:

1. 6.64 g (0.0239 mol) of 4-(3-cyclopentylpropionylamino)-benzoic acid, 2.78 ml (0.0248 mol) of N-methylmorpholine and 2.38 ml (0.0248 mol) of chloroformic acid ethyl ester.

2. 10.0 g (0.0286 mol) of ampicillin and 6.47 ml (0.0462 mol) of triethylamine.

Yield: 10.8 g (73.5%) of sodium D(−)-α-(4-[3-cyclopentylpropionylaminobenzoylamino-)]-benzylpencillin:

$C_{31}H_{35}N_4O_6SNa \cdot 3H_2O$ (668.7). Calculated. C, 55.68; H, 6.18; N, 8.38; S, 4.81. Found. C, 54.6; H, 6.1; N, 7.8; S 5.4.

β-Lactam content: 89.3%

B. 4-(3-Cyclopentylpropionylamino)-benzoic acid was prepared as described in Example 3 from 9.63 g (0.07 mol) of p-aminobenzoic acid and 12.4 g (0.077 mol) of 3-cyclopentylpropionyl chloride.

Yield: 12.0 g (65.6%)

$C_{15}H_{19}NO_3$ (261.3) Calculated. C, 68.95; H, 7.33; N, 5.36. Found. C, 68.8; H, 7.5;; N, 5.4.

EXAMPLE 10

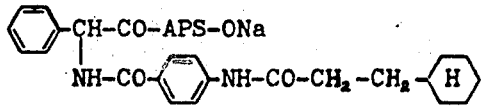

A. The penicillin was prepared as described in Example 2 from:

1. 6.6 g (0.024 mol) of 4-(3-cyclohexanepropionylamino)-benzoic acid, 2.78 ml (0.0248 mol) of N-methylmorpholine and 2.38 ml (0.0248 mol) of chloroformic acid ethyl ester.

2. 10.0 g (0.0286 mol) of ampicillin and 6.47 ml (0.0462 mol) of triethylamine.

Yield: 10.8 g (66.5%) of sodium D(−)-α-[4-(3-cyclohexanepropionylamino-benzoylamino)]-benzylpenicillin:

$C_{32}H_{37}N_4O_6SNa \cdot 2H_2O$ (664.8) Calculated. C, 57.82; H, 6.21; N, 8.43; S 4.83. Found: C, 56.8; H, 6.9; N, 8.0; S, 5.4.

β-Lactam content: 88.6%

B. 4-(3-Cyclohexanepropionylamino)-benzoic acid was prepared as described in Example 3 from 10.0 g (0.073 mol) of p-aminobenzoic acid and 14.0 g (0.08 mol) of 3-cyclohexanepropionyl chloride.

Yield: 15.8 g (79%)

$C_{16}H_{21}NO_3$(275.4) Caculated. C, 69.78; H, 7.69; N, 5.08. Found. C, 68.9; H, 7.0; N, 4.2.

EXAMPLE 11

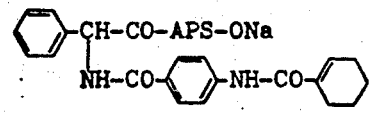

A. The penicillin was prepared as described in Example 2 from:

1. 7 g (0.0286 mol) of 4-(1-cyclohexene-1-carbonylamino)-benzoic acid, 3.2 ml (0.0286 mol) of N-methylmorpholine and 2.74 ml (0.0286 mol) of chloroformic acid ethyl ester.

2. 12 g (0.0343 mol) of ampicillin and 7.67 ml (0.0549 mol) of triethylamine.

Yield: 14.0 g (82%) of sodium D(=)-α-[4-(1-cyclohexene-1-carbonylamino-benzoylamino)]-benzylpencillin:

$C_{30}H_{31}N_4O_6SNa \cdot 2H_2O$ (634.7) Calculated. C, 56.78; H, 5.56; N, 8.83; S, 5.06. Found. C, 56.0; H, 5.6; N, 7.9; S, 5.3.

β-Lactam content: 88.0%

B. 4-(1-Cyclohexene-1-carbonylamino)-benzoic acid was prepared as described in Example 1 from 16.6 g (0.121 mol) of p-aminobenzoic acid with 22.0 g (0.152 mol) of 1-cyclohexene-1-carboxylic acid chloride and 21.3 ml (0.152 mol) of triethylamine. Recrystallization from THF/n-pentane.

Yield: 15.0 g (50.5%)

$C_{14}H_{15}NO_3$ (245.3) Calculated. C, 68.56; H, 6.16; N, 5.71. Found. C, 68.5; H, 6.2; N, 5.9.

EXAMPLE 12

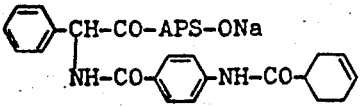

A. The penicillin was prepared as described in Example 2 from:

1. 5.85 g (0.0239 mol) of 4-(3-cyclohexene-1-carbonylamino)-benzoic acid, 2.69 mol (0.024 mol) of N-methylmorpholine and 2.3 ml (0.024 mol) of chloroformic acid ethyl ester.

2. 10 g (0.0286 mol) of ampicillin and 6.45 ml (0.046 mol) of triethylamine.

Yield: 8.8 g (60.7%) of sodium D(−)-α-[4-(3-cyclohexene-1-carbonylamino-benzoylamino)]-benzylpenicillin: $C_{30}H_{31}N_4O_6SNa \cdot 2H_2O$ (634.7) Calculated. C, 56.78; H, 5.56; N, 8.83; S, 5.06. Found. C, 56.5; H, 5.5; N, 7.7; S, 4.4.

β-Lactam content: 72.8%

B. 4-(3-Cyclohexene-1-carbonylamino)-benzoic acid was prepared as described in Example 3 from 12 g (0.0875 mol) of p-aminobenzoic acid and 13.9 g (0.0963 mol) of 3-cyclohexene-1-carboxylic acid chloride.

Yield: 17.2 g (80.5%)

$C_{14}H_{15}NO_3$ (245.3) Caculated. C, 68.56; H, 6.16; N, 5.71. Found. C, 67.2; H, 5.9; N, 5.2.

EXAMPLE 13

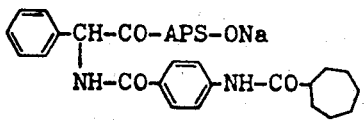

A. The penicillin was prepared as described in Example 2 from:

1. 7.0 g (0.0268 mol) of 4-cycloheptanecarbonylaminobenzoic acid, 3.0 ml (0.0268 mol) of N-methylmorpholine and 2.58ml (0.0268 mol) of chloroformic acid ethyl ester.

2. 11.2 g (0.0322 mol) of ampicillin and 7.2 ml (0.0515 mol) of triethylamine.

Yield: 12.0 g (73.0%) of sodium D(−)-α-(4-cycloheptanecarbonylamino-benzoylamino)-benzylpenicillin $C_{31}H_{35}N_4O_6SNa$ . $3H_2O$ (668.7) Calculated. C, 55.68; H, 6.18; N 8.38; S, 4.80. Found. C, 54.8; H, 6.2; N, 8.0; S, 5.4.

β-Lactam content: 92.3%

B. 4-Cycloheptanecarbonylamino-benzoic acid was prepared as described in Example 3 from 5.55 g (0.0405 mol) of p-aminobenzoic acid and 8.7 g (0.0425 mol) of cycloheptanecarboxylic acid chloride.

Yield: 9.9 g (94.0%)

$C_{15}H_{19}NO_3$ (261.3) Calculated. C, 68.95; H, 7.33; N, 5.36. Found. C, 67.0; H, 7.4; N, 5.2.

EXAMPLE 14

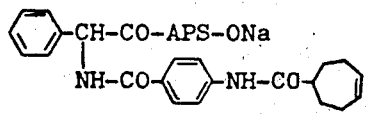

A. The penicillin was prepared as described in Example 2 from:

1. 6.0 g (0.0231 mol) of 4-(4-cycloheptene-1-carbonylamino)-benzoic acid, 2.69 ml (0.024 mol) of N-methylmorpholine and 2.3 ml (0.024 mol) of chloroformic acid ethyl ester.

2. 9.69 g (0.0277 mol) of ampicillin and 6.26 ml (0.0447 mol) of triethylamine.

Yield: 11.1 g (78.3%) of sodium D(−)-α-[4-(4-cycloheptene-1-carbonylamino-benzoylamino)]-benzylpenicillin:

$C_{31}H_{33}N_4O_6SNa$ . $2H_2O$ (648.7) Calculated. C, 57.40; H, 5.75; N, 8.64; S, 4.96. Found. C, 56.8; H, 6.1; N, 7.7; S 4.8.

β-Lactam content: 77.2%

B. 4-(4-Cycloheptene-1-carbonylamino)-benzoic acid was prepared as described in Example 3 from 4.45 g (0.0324 mol) of p-aminobenzoic acid and 5.7 g (0.0359 mol) of 4-cycloheptene-1-carboxylic acid chloride.

Yield: 6.3 g (75%)

$C_{15}H_{17}NO_3$ (259.3) Calculated. C, 69.48; H, 6.61; N, 5.40. Found. C, 67.8; H, 6.5; N 4.8.

EXAMPLE 15

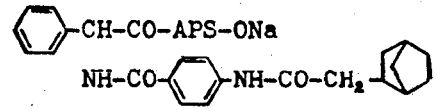

A. The penicillin was prepared as described in Example 2 from:

1. 6.53 g (0.0239 mol) of 4-[bicyclo(2,2,1)hept-2-yl-acetamido]-benzoic acid, 2.78 ml (0.0248 mol) of N-methylmorpholine and 2.38 ml (0.0248 mol) of chloroformic acid ethyl ester.

2. 10.0 g (0.0286 mol) of ampicillin and 6.47 ml (0.0467 mol) of triethylamine.

Yield: 9.3 g (62%) of sodium D(−)-α-[4-(2-norbornylacetamido-benzoylamino)]-benzylpenicillin:

$C_{32}H_{35}N_4O_6SNa$ . $3H_2O$ (680.8) Calculated. C, 56.56; H, 6.07; N, 8.23; S, 4.72. Found. C, 54.9; H, 5.9; N, 8.7; S, 5.7.

β-Lactam content: 100%

B. 4-[Bicyclo-(2,2,1)hept-2-yl-acetamido]-benzoic acid was prepared as described in Example 3 from 9.63 g (0.07 mol) of p-aminobenzoic acid and 13.2 g (0.077 mol) of bicyclo(2,2,1)hept-2-yl-acetyl chloride.

Yield: 17.4 g (91.2%)

$C_{16}H_{19}NO_3$ (273.3) Calculated. C, 70.32; H, 7.01; N, 5.12. Found. C, 67.1; H, 7.2; N, 5.0.

Table 3

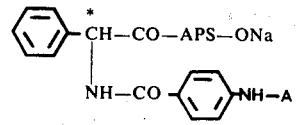

| Example No. A) Composition (Molecular weight) and B) Starting compound | A | yield % | β-Lactam content % | Analysis, % calculated/found | | | | |
|---|---|---|---|---|---|---|---|---|
| | | | | C | H | N | S | Cl |
| 16 A) $C_{31}H_{29}N_4O_7SNa$ 1 $H_2O$ (642.7) | CH₃O-⟨⟩-CO- | 71.4 | 66.3 | 57.94 58.2 | 4.86 5.7 | 8.72 8.4 | 4.99 4.9 | |
| B) $C_{15}H_{13}NO_4$ (271.3) | 4-(4-methoxybenzyl-amino)-benzoic acid | 84.5 | | 66.41 65.5 | 4.83 4.8 | 5.16 5.0 | | |
| 17 A) $C_{30}H_{26}FN_4O_6SNa$ 2 $H_2O$ (648.6) | F-⟨⟩-CO- | 66.6 | 100 | 55.56 55.3 | 4.66 5.6 | 8.62 8.6 | 4.95 5.6 | |

Table 3-continued $$\underset{NH-CO-\underset{}{\bigcirc}-NH-A}{\overset{*}{\bigcirc}-CH-CO-APS-ONa}$$

| A) Example No. Composition (Molecular weight) and B) Starting compound | A | yield % | β-Lactam content % | Analysis, % calculated/found |||||
|---|---|---|---|---|---|---|---|---|
| | | | | C | H | N | S | Cl |
| B) $C_{14}H_{10}FNO_3$ (259.2) | 4-(4-fluorobenzoylamino)-Benzoic acid 82.2 | | | 64.88 61.1 | 3.89 3.8 | 5.41 5.2 | | |
| 18 A) $C_{32}H_{31}N_4O_8SNi$ 2 $H_2O$ (690.7) | 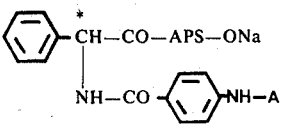 | 76.2 | 100 | 55.64 54.1 | 5.11 5.2 | 8.11 7.6 | 4.65 5.2 | |
| B) $C_{16}H_{15}NO_5$ (301.3) | 4-(3,5-dimethoxybenzoylamino)-benzoic acid 100 | | | 63.79 63.5 | 5.02 5.4 | 4.65 3.8 | | |
| 19 A) $C_{30}H_{25}N_6O_{10}SNa$ 1 $H_2O$ (702.6) | 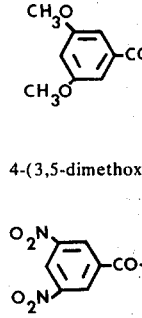 | 80.6 | 100 | 51.29 51.2 | 3.88 4.7 | 11.97 10.5 | 4.57 4.6 | |
| B) $C_{14}H_9N_3O_7$ (331.2) | 4-(3,5-dinitrobenzoylamino)-benzoic acid 50.0 | | | 50.77 51.7 | 2.74 4.0 | 12.68 13.2 | | |
| 20 A) $C_{30}H_{25}Cl_2N_4O_6SNa$ 2 $H_2O$ (699.549) | 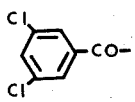 | 73.4 | 75.2 | 51.51 50.6 | 4.18 4.2 | 8.01 7.5 | 4.59 4.4 | 10.13 9.6 |
| B) $C_{14}H_9Cl_2NO_3$ (310.1) | 4-(3,5-dichlorobenzoylamino)-benzoic acid 64 | | | 54.23 53.1 | 2.93 2.9 | 4.52 3.9 | | 22.86 23.1 |
| 21 A) $C_{32}H_{31}N_4O_6SNa$ 2$H_2O$ (658.7) | 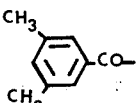 | 74 | 96.7 | 58.35 57.9 | 5.51 6.1 | 8.50 8.0 | 4.88 5.2 | |
| B) $C_{16}H_{15}NO_3$ (255.3) | 4-(3,5-dimethylbenzoylamino)-benzoic acid 91.8 | | | 71.36 68.8 | 5.61 5.6 | 5.20 4.3 | | |
| 22 A) $C_{33}H_{33}N_4O_9SNa$ 2 $H_2O$ (720.7) | 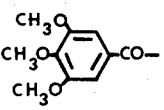 | 88.3 | 72.9 | 54.99 54.1 | 5.18 6.0 | 7.78 7.5 | 4.45 4.5 | |
| B) $C_{17}H_{17}NO_6$ (331.3) | 4-(3,4,5-trimethoxybenzoylamino)-benzoic acid 94.6 | | | 61.63 61.8 | 5.17 5.2 | 4.23 3.9 | | |
| 23 A) $C_{31}H_{26}F_3N_4O_6SNa$ 2 $H_2O$ (698.7) | 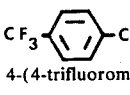 | 47.8 | 84.3 | 53.29 52.6 | 4.33 5.6 | 8.02 7.7 | 4.60 5.7 | |
| B) $C_{15}H_{10}F_3NO_3$ (309.2) | 4-(4-trifluoromethylbenzoylamino)-benzoic acid 58.0 | | | 58.25 58.2 | 3.26 3.6 | 4.53 4.2 | | |
| 24 A) $C_{31}H_{27}N_4O_8SNa$ 2 $H_2O$ (674.7) | 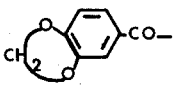 | 45.5 | 65.0 | 55.18 54.4 | 4.63 5.1 | 8.30 8.1 | 4.76 5.3 | |
| B) $C_{15}H_{11}NO_5$ (285.3) | 4-3,4-(methylenedioxy)-benzoylamino-benzoic acid 89 | | | 63.15 62.5 | 3.89 4.0 | 4.91 4.6 | | |
| 25 A) $C_{30}H_{27}N_4O_6SNa$ 2 $H_2O$ (630.7) | 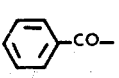 | 71.4 | 72.2 | 57.12 56.3 | 4.95 5.6 | 8.89 9.4 | 5.09 4.3 | |
| B) $C_{20}H_{14}N_4O_3$ (358.4) | 4-benzoylamino-benzoic acid 1-hydroxy-benzotriazole ester 84 | | | 67.02 67.0 | 5.63 4.2 | 15.65 15.8 | | |

Table 3-continued

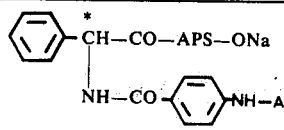

| Example No.<br>A) Composition (Molecular weight) and<br>B) Starting compound | A | yield % | β-Lactam content % | Analysis, % calculated/found | | | | |
|---|---|---|---|---|---|---|---|---|
| | | | | C | H | N | S | Cl |
| 26<br>A) $C_{30}H_{28}N_7O_8SNa$ · 2 $H_2O$ (635.6)<br>B) $C_{14}H_{10}N_4O_3$ (282.3) | <br>4(4-azidobenzoylamino)-benzoic acid | 81.8<br><br>83.9 | 90.5 | 53.64<br>53.0<br>59.57<br>59.6 | 4.50<br>4.8<br>3.58<br>3.4 | 14.60<br>14.8<br>19.85<br>20.4 | 4.78<br>4.8 | |

*C is in the D(−)- configuration

The compounds of Examples 16 and 26 were prepared by the acid chloride method and that of Example 25 was prepared via the activated ester 4-benzoylamino-benzoic acid 1-hydroxybenzotriazole ester. All other examples were synthesized by the mixed anhydride method.

EXAMPLE 27

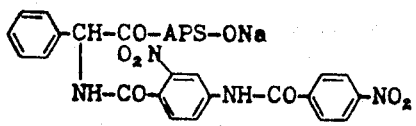

A. The above compound was prepared as described in Example 2 from:
1. 11.05 g (0.033 mol) of 4-(4-nitrobenzoylamino)-2-nitrobenzoic acid, 3.8 ml (0.034 mol) of N-methylmorpholine and 3.26 ml (0.034 mol) of chloroformic acid ethyl ester.
2. 14.0 g (0.04 mol) of ampicillin and 8.95 ml (0.064 mol) of triethylamine.

Yield: 8.3 g (36.6%) of sodium D(−)-α-[4-(4-nitrobenzoylamino)-2-nitrobenzoylamino)]-benzylpenicillin:

$C_{30}H_{25}N_6O_{10}SNa$ · 2 $H_2O$ (720.6) Calculated. C, 50.0; H, 4.06; N, 11.67; S, 4.45. Found. C, 49.6; H, 4.4; N, 11.5; S, 5.1.

β-Lactam content: 86.0%

B. 4-(4-Nitrobenzoylamino)-2-nitrobenzoic acid was prepared as described in Example 3 from 20.0 g (0.11 mol) of 4-amino-2-nitrobenzoic acid and 22.4 g (0.121 mol) of 4-nitrobenzoyl chloride. The product was reprecipitated from THF/H₂O.

Yield: 29.9 g (82.2%)
$C_{14}H_9N_3O_7$ (331.2) Calculated. C, 50.77; H, 2.74; N, 12.68. Found. C, 51.5; H, 3.5; N, 13.0.

EXAMPLE 28

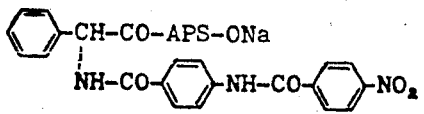

A. The above compound was prepared as described in Example 1 from:
15.0 g (0.0492 mol) of 4-(4-nitrobenzoylamino)-benzoyl chloride and 15.2 g (0.041 mol) of sodium ampicillin Yield: 20.5 g (78.5%) of sodium D(−)-α-[4-(4-nitrobenzoylamino)-benzoylamino]-benzylpenicillin $C_{30}H_{26}N_5O_8SNa$ · 2 $H_2O$ (675.7) Calculated. C, 53.32; H, 4.47; N, 10.37; S, 4.75. Found. C, 53.3; H, 4.4; N, 11.0; S, 5.4.

β-Lactam content: 88.8%

B. 4-(4-Nitrobenzoylamino)-benzoic acid was prepared as described in Example 3 from 15 g (0.11 mol) of PAB and 26.3 g (0.142 mol) of p-nitrobenzoyl chloride.

Yield: 30.1 g (96.2%)
$C_{14}H_{10}N_2O_5$ (286.2) Calculated. C, 58.76; H, 3.53; N, 9.78. Found. C, 58.6; H, 3.4; N, 9.7.

EXAMPLE 29

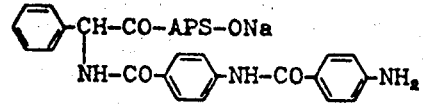

8.0 g (0.0125 mol) of sodium D(−)-α-[4-(4-nitrobenzoylamino-benzoylamino)]-benzylpenicillin were dissolved in 250 ml of absolute methanol and hydrogenated, in the presence of hydrogen, using as catalyst 30 g of palladium black on 90 g calcium carbonate, for 60 minutes at 0° to 50°C. The catalyst was added to the reaction solution in 3 portions at intervals of 20 minutes during the hydrogenation. The catalyst was separated from the solvent and the filtrate was gently concentrated to dryness in vacuo. The residue was dissolved in a little methanol and the solution was treated with absolute ether. The resulting precipitate was filtered off and thoroughly dried.

Yield: 7.0 g (91.9%) of sodium D(−)-α-[4-(4-aminobenzoylamino)-benzoylamino]-benzylpenicillin:
$C_{30}H_{28}N_5O_6SNa$ · 2H₂O (645.7)
Calculated. C, 55.81; H, 5.00; N, 10.85; S, 4.97. Found. C, 54.7; H, 5.7; N, 10.4; S, 5.2.

β-Lactam content: 62.8%

EXAMPLE 30

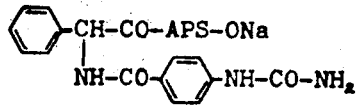

A. The above compound was prepared as described in Example 2 from:
1. 6 g (0.0334 mol) of 4-carbamoylaminobenzoic acid, 3.74 ml (0.0334 mol) of N-methylmorpholine and 3.72 ml (0.0334 mol) of chloroformic acid ethyl ester.
2. 18.6 g (0.0533 mol) of ampicillin and 12 ml (0.0858 mol) of triethylamine.

Yield: 10.8 g (61.1%) of sodium D(−)-α-(4-carbamoylaminobenzoylamino)-benzylpenicillin:

C₂₄H₂₄N₅O₆SNa . 2 H₂O (569.6)
Calculated. C, 50.61; H, 4.95; N, 12.29; S, 5.64.
Found. C, 50.7; H, 5.1; N, 10.7; S, 5.9.
β-Lactam content: 90.0%

B. 4-Carbamoyl-aminobenzoic acid was prepared from 20 g (0.146 mol) of PAB and 12.5 g (0.154 mol) of potassium cyanate. The reaction solution was stirred at 80° until a clear solution was just produced. The solution was left to stand overnight at room temperature and was then acidified with 2 N HCl. The precipitate was filtered off and recrystallized from hot ethanol, with admixture of water.
Yield: 21.8 g (83%)
C₈H₈N₂O₃ (180.2)
Calculated C, 53.32; H, 4.48; N, 15.54.
Found. C, 53.0; H, 4.6; N, 15.2.

EXAMPLE 31

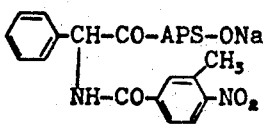

The above compound was prepared as described in Example 1 from 12 g (0.0324 mol) of sodium ampicillin and 7.08 g (0.354 mol) of 4-nitro-3-methylbenzoyl chloride.
Yield: 12.6 g (73.1%) of sodium D(−)-α-(4-nitro-3-methylbenzoylamino)-benzylpenicillin:
C₂₄H₂₃N₄O₇SNa . 1 H₂O (552.5)
Calculated. C, 52.17; H, 4.56; N, 10.14; S, 5.81.
Found. C, 52.0; H, 5.0; N, 9.8; S, 5.9.
β-Lactam content: 72.2%

EXAMPLE 32:

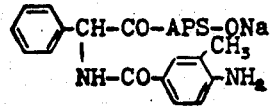

The above compound was prepared as described in Example 29 by catalytic hydrogenation of 5 g (0.0094 mol) of sodium D(−)-α-(4-nitro-3-methyl-benzoylamino)-benzylpenicillin.
Yield: 4.1 g (87.0%) of sodium D(−)-α-(4-amino-3-methylbenzoylamino)-benzyl-penicillin:
C₂₄H₂₅N₄O₅SNa . 2 H₂O (540.6)
Calculated. C, 53.32; H, 5.40; N, 10.37; S, 5.94.
Found. C, 52.7; H, 5.3; N, 9.5; S, 5.4.
β-Lactam content: 71.9%

EXAMPLE 33

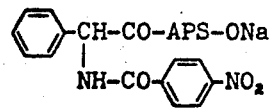

The above compound was prepared as described in Example 1 from 15 g (0.0403 mol) of sodium ampicillin and 9.75 g (0.0526 mol) of p-nitrobenzoyl chloride.
Yield: 19.2 g (91.5%) of sodium D(−)-α-(4-nitrobenzoylamino)-benzylpenicillin:
C₂₃H₂₁N₄O₇SNa . 1 H₂O (538.5)
Calculated. C, 51.30; H, 4.31; N, 10.40; S, 5.96.
Found. C, 52.0; H, 5.2; N, 9.4; S, 5.5.
β-Lactam content: 76.8%

EXAMPLE 34

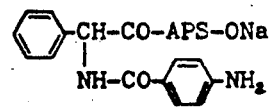

The above compound was prepared as described in Example 29 by catalytic hydrogenation of 8.0 g (0.0154 mol) of sodium D(−)-α-(4-nitro-benzoylamino)-benzylpenicillin.
Yield: 6.0 g (79.8%) of sodium D(−)-α-(4-aminobenzoylamino)-benzylpenicillin
C₂₃H₂₃N₄O₅SNa . 1 H₂O (508.5)
Calculated. C, 54.33; H, 4.96; N, 11.02; S, 6.31.
Found. C, 55.7; H, 6.0; N, 9.5; S, 5.9.
β-Lactam content: 68.7%

Table 4

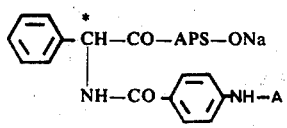

| Example No. A) Composition (molecular weight) and B) Starting substance | A | Yield % | β-Lactam content % | Analysis, % calculated/found C | H | N | S |
|---|---|---|---|---|---|---|---|
| 35 A) C₃₂H₂₉N₄O₆SNa .3 H₂O (674.7) | ⟨⟩-CH=CH-CO- | 80.4 | 95.2 | 56.97 / 56.2 | 5.23 / 5.8 | 8.30 / 8.2 | 4.75 / 5.5 |
| B) C₁₆H₁₃NO₃ (267.3) | 4-cinnamoyl-aminobenzoic acid 97.4 | | | 71.90 / 71.6 | 4.90 / 4.7 | 5.24 / 4.7 | |
| 36 A) C₂₅H₂₄N₇O₆SNa .1 H₂O (591.6) | N₃—CH₂—CO— | 78.0 | 87.5 | 50.76 / 50.6 | 4.43 / 4.7 | 16.54 / 16.6 | 5.42 / 5.4 |
| B) C₉H₈N₄O₃ (220.2) | 4-azidoacetyl-aminobenzoic acid 98.2 | | | 49.09 / 48.8 | 3.67 / 3.5 | 25.45 / 25.0 | |
| 37 A) C₂₆H₂₆N₇O₆SNa .1 H₂O (587.6) | N₃\⟩CH—CO— CH₃/ | 88.8 | 71.0 | 51.57 / 51.6 | 4.66 / 5.6 | 16.19 / 15.3 | 5.30 / 4.9 |
| B) C₁₀H₁₀N₄O₃ (234.2) | 4-(2-azidopropionyl)-aminobenzoic acid 86.0 | | | 51.31 / 51.3 | 4.31 / 4.2 | 23.92 / 23.3 | |

3,982,011

Table 4-continued

*CH—CO—APS—ONa with NH—CO—C₆H₄—NH—A

| Example No. A) Composition (molecular weight) and B) Starting substance | A | Yield % | β-Lactam content % | C | H | N | S |
|---|---|---|---|---|---|---|---|
| 38 A) C₂₆H₂₆N₇O₆SNa .2 H₂O (623.6) B) C₁₀H₁₀N₄O₃ (234.2) | N₃—CH₂—CH₂—CO— 4-azidopropionyl-aminobenzoic acid | 81.0 89 | 96 | 50.08 50.3 51.29 51.3 | 4.85 4.6 4.31 4.2 | 15.72 14.6 23.92 22.5 | 5.15 5.5 |
| 39 A) C₂₈H₃₀N₇O₆SNa .2 H₂O (651.7) B) C₁₂H₁₄N₄O₃ (262.3) | N₃—CH₂—C(CH₃)₂—CO— 4-(3-aziod-2,2-dimethyl-propionyl)-amino-benzoic acid | 76.7 73.8 | 94.8 | 51.60 50.7 54.95 54.0 | 5.26 6.0 5.38 5.4 | 15.05 13.1 21.36 20.7 | 4.92 5.3 |
| 40 A) C₂₇H₂₈N₇O₆SNa .1 H₂O (619.6) B) C₁₁H₁₂N₄O₃ (248.2) | N₃>CH—CH₂—CO— CH₃ 4-(3-azido-butyric acid amido)-benzoic acid | 68.1 70.2 | 81.6 | 52.34 52.2 53.24 53.6 | 4.88 5.3 4.88 5.0 | 15.82 13.1 22.57 20.2 | 5.18 5.8 |
| 41 A) C₂₄H₂₃N₄O₆SNa .3 H₂O (572.6) B) C₈H₇NO₃ (165.15) | H—CO— 4-formyl-aminobenzoic acid | 63.4 53.1 | 53.9 88.3 | 50.35 50.0 58.25 57.9 | 5.11 5.6 4.25 4.3 | 9.79 8.4 8.5 8.3 | 5.6 5.5 |
| 42 A) C₂₆H₂₇N₄O₇SNa .2 H₂O (598.6) B) C₁₀H₁₁NO₄ (209.2) | CH₃O—CH₂—CO— 4-methoxyacetamido-benzoic acid | 83.8 46.6 | 88 | 52.17 52.9 57.42 56.9 | 5.22 5.4 5.30 5.2 | 9.36 9.0 6.69 6.2 | 5.36 5.4 |
| 43 C₂₄H₂₅N₄O₅SNa . 3H₂O (558.6) | CH₃— | 78.3 | 94.0 | 51.61 51.4 | 5.59 5.7 | 10.03 9.4 | 5.75 6.3 |
| 44 A) C₂₅H₂₆N₅O₆SNa . 2H₂O (583.6) | CH₃—NH—CO— | 67.2 | 87.3 | 51.46 52.0 | 5.18 6.3 | 11.99 10.5 | 5.50 6.0 |
| 45 A) C₃₀H₂₈N₅O₆SNa . 2H₂O (609.6) B) C₁₄H₁₂N₂O₃ (256.4) | C₆H₅—NH—CO— p-phenylureido-benzoic acid | 90.8 78.8 | 90.7 | 55.81 55.9 65.59 66.1 | 5.00 5.9 4.72 4.6 | 10.85 10.3 10.92 10.9 | 4.97 5.6 |
| 46 A) C₃₀H₂₇FN₅O₆SNa . 2 H₂O (663.7) B) C₁₄H₁₁FN₂O₃ (274.3) | F—C₆H₄—NH—CO— 4-(4-fluorophenyluredio)-benzoic acid | 82.5 88 | 89.8 | 54.30 54.5 61.30 60.7 | 4.71 5.3 4.04 4.1 | 10.55 9.5 10.21 10.0 | 4.84 4.7 |
| 47 A) C₂₅H₂₆N₅O₅S₂Na . 2 H₂O (599.7) B) C₉H₁₀N₂O₂S (210.3) | CH₃—NH—CS— 4-methylthioureido-benzoic acid | 70.6 | 86.8 | 50.07 50.6 51.41 51.7 | 5.04 5.1 4.79 5.0 | 11.68 10.9 13.32 13.3 | 10.71 9.3 15.25 14.6 |
| 48 A) C₂₈H₂₅N₄O₆S₂Na . 2 H₂O (636.7) B) C₁₂H₉NO₃S (247.3) | (thiophen-2-yl)—CO— 4-(thiophene-2-carbonylamino)-benzoic acid | 68.5 69.8 | 88.1 | 52.82 52.3 58.28 57.6 | 4.59 4.6 3.67 3.7 | 8.81 8.9 5.66 5.5 | 10.08 10.2 12.96 12.8 |

Notes: Examples 35, 39, 40, 41, 42, 43, 46, 47 and 48 used the mixed anhydride method (as described in Example 2) and Examples 36, 37, 38, 44 and 45 the acid chloride process.

* C is in the D(−)- configuration

Table 5

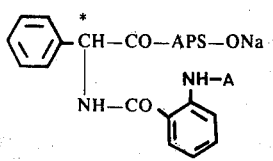

| Example No. A) Composition (molecular weight) and B) Starting compound | A | Yield % | β-Lactam content % | Analysis, % calculated/found | | | |
|---|---|---|---|---|---|---|---|
| | | | | C | H | N | S |
| 49 A) C₂₇H₂₇N₄O₆SNa . 2H₂O (594.6) | ▷-CO- | 50.5 | 69.1 | 54.54 52.9 | 5.25 6.3 | 9.42 8.0 | 5.40 6.2 |
| B) C₁₁H₁₁NO₃ (205.2) | 2-cyclopropanecarbonylamino-benzoic acid 54.7 | | | 64.39 63.7 | 5.40 5.2 | 6.82 7.4 | |
| 50 A) C₂₈H₂₉N₄O₆SNa. 2H₂O (608.6) | ◇-CO- | 41.7 | 85.3 | 55.26 54.7 | 5.46 5.6 | 9.2 8.7 | 5.28 5.7 |
| B) C₁₂H₁₃NO₃ (219.2) | 2-cyclobutanecarbonylamino-benzoic acid 69.7 | | | 65.75 65.3 | 5.98 6.0 | 6.39 6.3 | |

The compounds of Examples 49 and 50 were prepared according to the mixed anhydride method.
* C is in the D(−)- configuration Table 6

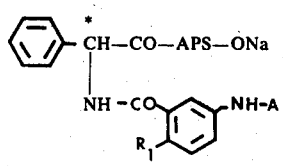

(Method of synthesis: as described in Example 2)

| Example No. A) Composition (molecular weight) and B) Starting compound | A | Yield % | β-Lactam content % | Analysis, % calculated/found | | | | |
|---|---|---|---|---|---|---|---|---|
| | | | | C | H | N | S | Cl |
| 51 A) C₂₇H₂₇N₄O₆SNa .2 H₂O (594.6) | ▷-CO- R₁: H | 86.7 | 81.9 | 54.54 54.6 | 5.25 6.2 | 9.42 9.6 | 5.40 6.4 | |
| B) C₁₁H₁₁NO₃ (205.216) | 3-cyclopropanecarbonylamino-benzoic acid 89.8 | | | 64.39 63.8 | 5.40 5.6 | 6.82 6.9 | | |
| 52 A) C₂₈H₂₈ClN₄O₆SNa .2 H₂O (643.1) | ◇-CO- R₁: Cl | 78.6 | 88.7 | 52.29 53.1 | 5.02 5.5 | 8.71 8.0 | 4.99 4.8 | 5.51 5.2 |
| B) C₁₂H₁₂ClNO₃ (253.7) | 3-cyclobutanecarbonylamino-6-chloro-benzoic acid 70 | | | 56.82 56.3 | 4.77 4.8 | 5.52 5.3 | | 13.97 14.0 |
| 53 A) C₂₇H₂₆ClN₄O₆SNa .1 H₂O (611.0) | ▷-CO- R₁: Cl | 82.5 | 88.8 | 53.08 52.8 | 4.62 5.6 | 9.17 8.1 | 5.25 5.4 | 5.80 5.1 |
| B) C₁₁H₁₀ClNO₃ (239.7) | 3-cyclopropanecarbonylamino-6-chlorobenzoic acid 75.7 | | | 55.12 55.0 | 4.21 4.3 | 5.85 5.8 | | 14.79 14.4 |

* C is in the D(−)- configuration

Table 7

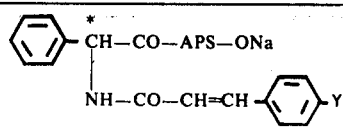

| Example No. A) Composition (molecular weight) and B) Starting compound | Y | Yield % | β-Lactam content % | Analysis, % calculated/found | | | |
|---|---|---|---|---|---|---|---|
| | | | | C | H | N | S |
| 54 $C_{25}H_{23}N_4O_7SNa \cdot 2H_2O$ (582.6) | $NO_2-$ | 82.4 | 82.5 | 51.54 52.9 | 4.67 5.6 | 9.62 9.1 | 5.51 5.6 |
| 55 A) $C_{26}H_{25}N_4O_8SNa \cdot 2 H_2O$ (580.6) B) $C_{10}H_9NO_3$ (191.2) | H—CO—NH— 4-formyl-aminocinnamic acid | 76.5 34.9 | 91.8 | 53.79 53.8 62.82 62.9 | 5.03 5.4 4.74 4.8 | 9.65 9.4 7.32 7.4 | 5.53 5.5 |
| 56 A) $C_{29}H_{29}N_4O_6SNa \cdot 2 H_2O$ (620.7) B) $C_{13}H_{13}NO_3$ (231.3) | ▷-CO-NH- 4-cyclopropanecarbonylamino-cinnamic acid | 80.5 68.4 | 77.9 | 56.12 56.0 67.54 66.9 | 5.36 5.5 5.66 5.8 | 9.01 8.9 6.05 6.0 | 5.17 5.3 |
| 57 A) $C_{30}H_{31}N_4O_6SNa \cdot 2 H_2O$ (634.7) B) $C_{14}H_{15}NO_3$ (245.3) | ◇-CO-NH- 4-cyclobutanecarbonylaminocinnamic-acid | 78.2 81.0 | 83.7 | 56.78 57.5 68.56 67.9 | 5.56 5.5 6.16 6.3 | 8.83 9.3 5.71 5.6 | 5.06 5.3 |

Notes:
The compound of Example 54 was prepared via the acid chloride method and those of Examples 55, 56 and 57 were prepared via the mixed anhydride method

* C is in the D(−)- configuration

Table 8

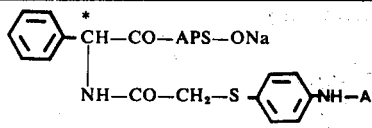

| Example No. A) Composition (molecular weight) and B) Starting compound | A | Yield % | β-Lactam content % | Analysis, % calculated/found | | | |
|---|---|---|---|---|---|---|---|
| | | | | C | H | N | S |
| 58 A) $C_{34}H_{35}N_4O_9S_2Na \cdot 2 H_2O$ (766.8) B) $C_{18}H_{19}NO_6S$ (377.4) | $CH_3O$-, $CH_3O$-⌬-CO- , $CH_3O$- 4-(3,4,5-trimethoxybenzoylamino-phenylthio)]-acetic acid | 97 82.5 | 96.8 | 53.25 54.0 57.29 56.1 | 5.13 5.5 5.08 5.0 | 7.31 6.9 3.72 3.3 | 8.37 8.4 8.50 8.0 |
| 59 A) $C_{25}H_{25}N_4O_8S_2Na \cdot 1 H_2O$ (582.6) B) $C_9H_9NO_3S$ (211.2) | H—CO— (p-formylamino-phenylthio)-acetic acid | 75.5 50.5 | 100 | 51.54 51.9 51.18 50.9 | 4.67 5.1 4.30 4.4 | 9.62 8.7 6.63 6.7 | 11.00 10.5 15.18 14.9 |
| 60 A) $C_{28}H_{29}N_4O_6S_2Na \cdot 1 H_2O$ (622.7) B) $C_{12}H_{13}NO_3S$ (251.3) | ▷-CO— (p-cyclopropanecarbonylaminophenyl-thio)-acetic acid | 87.5 76.9 | 81.5 | 54.01 54.0 57.35 56.5 | 5.02 5.7 5.21 5.0 | 9.00 8.5 5.57 5.6 | 10.23 10.2 12.75 12.8 |
| 61 A) $C_{29}H_{31}N_4O_6S_2Na \cdot 1 H_2O$ (636.7) B) $C_{13}H_{15}NO_3S$ (265.3) | ◇-CO— (p-cyclobutanecarbonylamino-phenylthio)-acetic acid | 73.8 58.6 | 98.5 | 54.71 54.7 58.85 58.9 | 5.22 5.6 5.70 5.7 | 8.80 8.7 5.28 4.6 | 10.08 10.1 12.08 11.09 |
| 62 A) $C_{31}H_{33}N_4O_6SNa \cdot 1 H_2O$ (662.8) B) $C_{15}H_{17}NO_3S$ (291.4) | ⬠-$CH_2$-CO— [p-(2-cyclopentene-1-acetyl)-amino-phenylthio]-acetic acid | 52.3 69.5 | 91.1 | 56.18 56.6 61.83 61.0 | 5.32 5.6 5.88 5.4 | 8.45 8.0 4.81 4.5 | 9.69 9.6 11.00 11.0 |

Note:
All 5 Examples used the mixed anhydride method.

* C is in the D(−)- configuration

Table 9

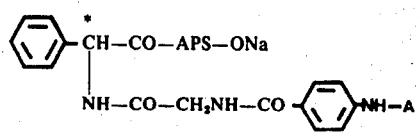

| Example No. A) Composition (molecular weight) and B) Starting compound | A | Yield % | β-Lactam content % | Analysis, % calculated/found C | H | N | S |
|---|---|---|---|---|---|---|---|
| 63 A) $C_{25}H_{28}N_5O_7SNa$ .2 $H_2O$ (611.6) B) $C_{10}H_{10}N_2O_4$ (222.2) | H—CO— N-(p-formylaminobenzoyl)-glycine | 66.9 45.3 | 91.5 | 51.06 52.0 54.05 53.7 | 4.94 4.7 4.54 4.8 | 11.45 11.0 12.55 12.4 | 5.25 6.2 |
| 64 A) $C_{29}H_{30}N_5O_7SNa$ .1 $H_2O$ (633.7) B) $C_{13}H_{14}N_2O_4$ (262.3) | ▷—CO— N-(p-cyclopropanecarbonylamino- benzoyl)-glycine | 74.0 67.4 | 78.1 | 54.97 55.5 59.53 59.2 | 5.08 6.6 5.38 5.4 | 11.05 9.7 10.68 10.5 | 5.07 4.5 |
| 65 A) $C_{30}H_{32}N_5O_7SNa$ .2 $H_2O$ (665.7) B) $C_{14}H_{16}N_2O_4$ (276.3) | ▢—CO— N-(p-cyclobutanecarbonylamino- benzoyl)-glycine | 58.6 68.4 | 70.2 | 54.23 54.8 60.86 61.1 | 5.45 5.9 5.83 5.8 | 10.52 10.1 10.14 10.3 | 4.82 4.7 |

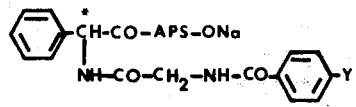

| Example No. A) Composition B) Starting compound | A | Yield % | β-Lactam content % | C | H | N | S |
|---|---|---|---|---|---|---|---|
| 66 A) $C_{31}H_{34}N_5O_7SNa$ .2 $H_2O$ (679.7) B) $C_{15}H_{18}N_2O_4$ (290.3) | ⬠—CO—NH— N-(p-cyclopentanecarbonylamino- benzoyl)-glycine | 96.1 65.1 | 89.2 | 54.78 54.2 62.06 61.4 | 5.63 5.6 6.25 5.9 | 10.30 10.4 9.65 9.4 | 4.73 5.0 |
| 67 A) $C_{32}H_{34}N_5O_7SNa$ .1 $H_2O$ (673.7) B) $C_{16}H_{18}N_2O_4$ (302.3) | ⬡—CO—NH— N-[p-(1-cyclohexene-1-1carbonyl)- aminobenzoyl]-glycine | 78.5 61.7 | 93.5 | 57.05 56.6 63.58 62.8 | 5.38 6.5 6.00 5.7 | 10.40 9.8 9.27 8.8 | 4.77 4.8 |
| 68 A) $C_{25}H_{24}N_7O_6SNa$ .1 $H_2O$ (591.6) B) $C_9H_8N_4O_3$ (220.2) | $N_3$— N-(p-azidobenzoyl)-glycine | 89.8 31.8 | 88.1 | 50.76 51.6 49.09 49.1 | 4.30 5.1 3.67 3.7 | 16.08 15.6 25.45 25.4 | 5.27 5.2 |
| 69 A) $C_{25}H_{24}N_5O_8SNa$ .1 $H_2O$ (595.6) B) $C_9H_8N_2O_5$ (224.2) | $NO_2$— N-(p-nitrobenzoyl)-glycine | 74.3 56.2 | 77 | 50.42 50.0 48.22 48.2 | 4.40 4.9 3.6 3.5 | 11.76 11.5 12.50 11.7 | 5.39 5.5 |
| 70 $C_{25}H_{26}N_5O_6SNa$ .2 $H_2O$ (583.6) | $NH_2$— | 93.0 | 58.7 | 51.46 51.5 | 5.18 5.4 | 12.00 10.9 | 5.50 5.5 |

Notes:
Examples 63 to 69 used the mixed anhydride synthesis. Example 70 used catalytic hydrogenation (as described in Example 29) of the compound of Example 69.

* C is in the D(—)- configuration

Table 10

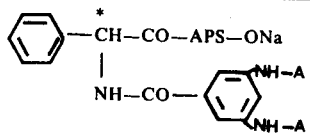

| Example No.<br>A) Composition (molecular weight) and<br>B) Starting compound | A | Yield % | β-Lactam content % | Analysis, % calculated/found | | | |
|---|---|---|---|---|---|---|---|
| | | | | C | H | N | S |
| 71<br>A) $C_{25}H_{24}N_5O_7SNa$<br>.1 $H_2O$ (579.6)<br>B) $C_9H_8N_2O_4$ (208.2) | H—CO—<br><br>3,5-bis-formylamino-benzoic acid | 75.4<br><br><br>86 | 90.3 | 51.81<br>51.6<br>51.92<br>51.1 | 4.53<br>4.9<br>3.88<br>3.9 | 12.08<br>11.5<br>13.46<br>13.0 | 5.54<br>5.5 |
| 72<br>A) $C_{31}H_{32}N_5O_7SNa$<br>.2 $H_2O$ (677.7)<br>B) $C_{15}H_{16}N_2O_4$ (288.3) | ▷-CO—<br><br>3,5-bis-(cyclopropanecarbonyl-amino)benzoic acid | 66.7<br><br><br>77.0 | 87.5 | 54.94<br>54.8<br>62.49<br>61.5 | 5.35<br>5.7<br>5.59<br>6.5 | 10.33<br>8.8<br>9.72<br>8.0 | 4.74<br>5.4 |
| 73<br>A) $C_{33}H_{36}N_5O_7SNa$<br>.2 $H_2O$ (705.8)<br>B) $C_{17}H_{20}N_2O_4$ (316.4) | ◇-CO—<br><br>3,5-bis-(cyclobutanecarbonyl-amino)-benzoic acid | 71.5<br><br><br>97.0 | 94.7 | 56.16<br>55.4<br>64.54<br>63.0 | 5.72<br>5.7<br>6.37<br>6.4 | 9.93<br>8.6<br>8.86<br>7.7 | 4.55<br>5.3 |

All three compounds (71–73) were prepared via the mixed anhydride method.

* C is in the D(—)- configuration

Table 11

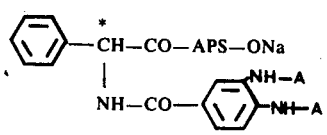

| Example No.<br>A) Composition (molecular weight) and<br>B) Starting compound | A | Yield % | β-Lactam content % | Analysis, % calculated/found | | | |
|---|---|---|---|---|---|---|---|
| | | | | C | H | N | S |
| 74<br>A) $C_{25}H_{24}N_5O_7SNa$<br>.2 $H_2O$ (597.6)<br>B) $C_9H_8N_2O_4$ (208.2) | H—CO—<br><br>3,4-bis-formylamino-benzoic acid | 45.4<br><br><br>79.6 | 100 | 50.25<br>49.5<br>51.92<br>50.7 | 4.72<br>4.0<br>3.88<br>3.8 | 11.72<br>9.6<br>13.46<br>12.8 | 5.37<br>6.8 |
| 75<br>A) $C_{31}H_{32}N_5O_7SNa$<br>.2 $H_2O$ (677.7)<br>B) $C_{15}H_{16}N_2O_4$ (288.3) | ▷-CO—<br><br>3,4-bis-(cyclopropanecarbonyl-amino)-benzoic acid | 71.8<br><br><br>41.4 | 100 | 54.94<br>54.1<br>62.49<br>61.1 | 5.35<br>5.4<br>5.59<br>5.7 | 9.33<br>9.5<br>9.72<br>10.1 | 4.74<br>5.2 |

Both compounds (74 and 75) were prepared via the mixed anhydride method.

* C is in the D(—)- configuration

EXAMPLE 76:

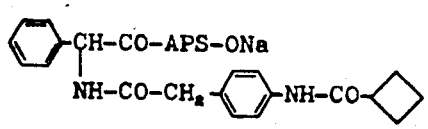

A. The above compound was prepared as described in Example 2 from:

1. 5.78 g (0.0248 mol) of (4-cyclobutanecarbonylaminophenyl)-acetic acid, 2.8 ml (0.025 mol) of N-methylmorpholine and 2.4 ml (0.025 mol) of chloroformic acid ethyl ester.

2. 10.4 g (0.0298 mol) of ampicillin and 6.68 ml (0.0477 mol) of triethylamine.

Yield: 13.1 g (90.3%) sodium D(—)-α-[(4-cyclobutanecarbonylaminophenyl)-acetamido]-benzylpenicillin:

$C_{29}H_{31}N_4O_6SNa$ . 2 $H_2O$ (622.7) Calculated. C,55.95; H,5.66; N,9.00; S,5.15. Found. C,56.5; H,5.8; N,9.7; S,5.5.

β-Lactam content: 87.8%

B. (4-Cyclobutanecarbonylaminophenyl)-acetic acid was prepared as described in Example 3 from 7.0 g (0.0464 mol) of p-aminophenyl)-acetic acid and 6.6 g (0.0557 mol) of cyclobutanecarboxylic acid chloride.

Yield: 10.0 g (83.3%)

$C_{13}H_{15}NO_3$ (233.3) Calculated. C,66.93; H,6.48; N,6.00. Found. C,66.5; H,6.3; N,5.7.

EXAMPLE 77

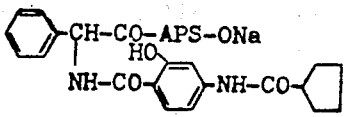

A. The above compound was prepared similarly to that of Example 26 via the N-hydroxy-benzotriazole method [W. Konig and R. Geiger, Chem. Ber. 103, 788–798 (1970)] from the following components:

1. 4.7 g (0.0188 mol) of 4-cyclopentanecarbonylamino-2-hydroxybenzoic acid, 2.69 g (0.0198 mol) of 1-hydroxy-benzotriazole and 4.17 g (0.0202 mol) of dicyclohexylcarbodiimide (DCC).

2. 7.86 g (0.0225 mol) of ampicillin and 5.53 ml (0.0394 mol) of triethylamine.

Yield: 8.4 g (74.0%) of sodium D(—)-α-(4-cyclopentanecarbonylamino-2-hydroxybenzoylamino)-benzyl-penicillin:

$C_{29}H_{31}N_4O_7SNa$ . 2 $H_2O$ (638.7) Calculated. C, 54.54; H, 5.52; N, 8.77; S, 5.03. Found. C, 54.3; H, 5.8; N, 9.6; S, 4.8.

β-Lactam content: 73.8%.

| Activity against E. coli 14: | 2 – 4 U/ml |
| Activity against Proteus vulg. 1017: | 8 – 16 U/ml |
| Activity against Psdm. aerug. Walter: | 8 – 16 U/ml |
| Activity against Klebs. 63: | 32 – 64 U/ml |
| Activity against Staph. aureus 1756: | 32 – 64 U/ml |

B. 4-Cyclopentanecarbonylamino-2-hydroxy-benzoic acid was prepared as described in Example 3 from 8 g (0.0379 mol) of 4-amino-2-hydroxy-benzoic acid (sodium salt, with 2 mols of $H_2O$) and 5.28 g (0.0398 mol) of cyclopentanecarboxylic acid chloride.

Yield: 7.2 g (76.3%)

$C_{13}H_{15}NO_4$ (249.3) Calculated. C, 62.63; H, 6.06; N, 5.62. Found. C, 62.7; H, 6.3; N, 5.5.

EXAMPLE 78

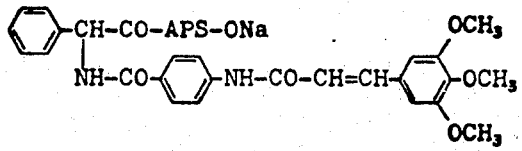

A. The penicillin was prepared as described in Example 2 from:

1. 5.6 g (0.0157 mol) of 4-(3,4,5-trimethoxycinnamoylamino)-benzoic acid, 1.83 ml (0.0163 mol) of N-methylmorpholine and 1.57 ml (0.0163 mol) of chloroformic acid ethyl ester.

2. 6.58 g (0.0188 mol) of ampicillin and 4.26 ml (0.0304 mol) of triethylamine.

Yield: 9.3 g (83.4%) of sodium D(—)-α-[4-(3,4,5-trimethoxycinnamoylamino-benzoylamino)]-benzyl-penicillin:

$C_{35}H_{35}N_4O_9SNa$ . 2 $H_2O$ (746.8) Calculated. C, 56.29; H, 5.27; N, 7.51; S, 4.30. Found. C, 54.9; H, 5.7; N, 6.8; S, 4.7.

β-Lactam content: 90.2%

| Activity against E. coli 14: | 2 – 4 U/ml |
| Activity against Proteus vulg. 1017: | 128 – 256 U/ml |
| Activity against Psdm. aerug. Walter: | 32 – 64 U/ml |
| Activity against Klebs. 63: | 32 – 64 U/ml |

B. 4-(3,4,5-trimethoxycinnamoylamino)-benzoic acid was prepared as described in Example 3 from 3.3 g (0.0241 mol) of PAB and 6.8 g (0.0265 mol) of 3,4,5-trimethoxycinnamoyl chloride.

Yield: 5.6 g (65.1%), recrystallization from THF/n-petane $C_{19}H_{19}NO_6$ (357.4) Calculated. C, 63.85; H, 5.35; N, 3.91. Found. C, 62.5; H, 5.4; N, 3.3.

EXAMPLE 79

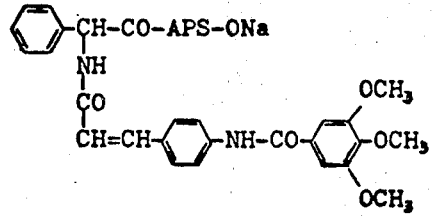

A. The above compound was prepared as described in Example 2 from:

1. 6.1 g (0.0171 mol) of 4-(3,4,5-trimethoxybenzoylamino)-cinnamic acid, 1.98 ml (0.0177 mol) of N-methylmorpholine and 1.7 ml (0.0177 mol) of chloroformic acid ethyl ester.

2. 7.14 g (0.0204 mol) of ampicillin and 4.62 ml (0.033 mol) of triethylamine.

Yield: 10.3 g (85%) of sodium D(—)-α-[4-(3,4,5-trimethoxybenzoylamino-cinnamoylamino)]-benzyl-penicillin:

$C_{35}H_{35}N_4O_9SNa$ . 2 $H_2O$ (746.8) Calculated. C, 56.29; H, 5.27; N, 7.51; S, 4.30. Found. C, 56.0; H, 6.0; N, 7.0; S, 4.5.

β-Lactam content: 89.7%

| Activity against E. coli 14: | 1 – 2 | U/ml |
| Activity against Proteus vulg. 1017: | 128 – 256 | U/ml |
| Activity against Psdm. aerug. F. 41: | 8 – 16 | U/ml |
| Activity against Klebs. 63: | 32 – 64 | U/ml |
| Activity against Staph. aureus 133: | <1 | U/ml |

B. 4-(3,4,5-Trimethoxybensoylamino)-cinnamic acid was prepared as described in Example 3 from 5 g (0.0271 mol) of p-aminocinnamic acid hydrochloride and 3,4,5-trimethoxybenzoyl chloride.

Yield: 6.8 g (70.2%)

$C_{19}H_{19}NO_6$ (357.4) calculated. C, 63.85; H, 5.35; N, 3.91. Found. C, 63.6; H, 5.4; N, 3.2.

EXAMPLE 80

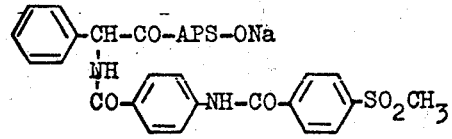

A. The above compound was prepared as described in Example 2 from:

1. 3.6 g (0.0113 mol) of 4-(p-methylsulphonyl-benzoylamino)-benzoic acid, 1.4 ml (0.0125 mol) of N-methylmorpholine and 1.2 ml (0.0125 mol) of chloroformic acid ethyl ester.

2. 4.75 g (0.0136 mol) of ampicillin and 3.05 ml (0.0218 mol) of triethylamine.

Yield: 5.6 g (70%) of sodium D(−)-α-[4-(p-methylsulphonylbenzoylamino)-benzoylamino]-benzylpenicillin $C_{31}H_{29}N_4O_8S_2Na \cdot 2 H_2O$ (708.7)

Calculated. C, 52.53; H, 4.70; N, 7.92; S, 9.06. Found. C, 52.1; H, 5.1; N, 6.3; S, 8.9.

β-Lactam content: 72.9%

| Activity against E. coli 14: | 4 – 8 | U/ml |
| Activity against Proteus vulg. 1017: | 128 – 256 | U/ml |
| Activity against Psdm. aerug. F 41: | 32 – 64 | U/ml |
| Activity against Klebs. 63: | 32 – 64 | U/ml |
| Activity against Staph. aureus 133: | <1 | U/ml |

EXAMPLE 81

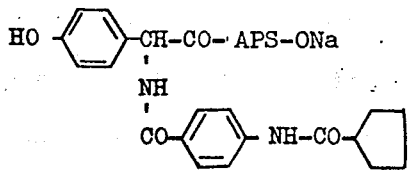

A. The above compound was prepared as described in Example 1 from:

7.0 g (0.0168 mol) of p-hydroxyampicillin [D(−)-(α-amino-p-hydroxyphenylacetylamino)-penicillin] and 5.5 g (0.0219 mol) of 4-cyclopentanecarbonylaminobenzoyl chloride (see Example 7C).

Yield: 5.9 (51.8%) of sodium D(−)-α-[4-cyclopentanecarbonylamino-benzoylamino]- (p-hydroxybenzyl)-penicillin:

$C_{29}H_{31}N_4O_7SNa \cdot 3 H_2O$ (656.7) Calculated. C, 53.04; H, 5.68; N, 8.53; S, 4.89. Found. C, 52.3; H, 5.8; N, 8.4; S, 6.6.

β-Lactam content: 79.6%

| Activity against E. coli 14: | 4 – 8 | U/ml |
| Activity against Proteus vulg. 1017: | >256 | U/ml |
| Activity against Psdm. aerug. F 41: | 32 – 64 | U/ml |
| Activity against Klebs. 63: | 128 – 256 | U/ml |
| Activity against Staph. aureus 133: | <1 | U/ml |

What is claimed is:

1. A pharmaceutical composition for combatting infections in animals and humans comprising an antibacterially effective amount of a compound selected from the group consisting of a penicillin of the formula:

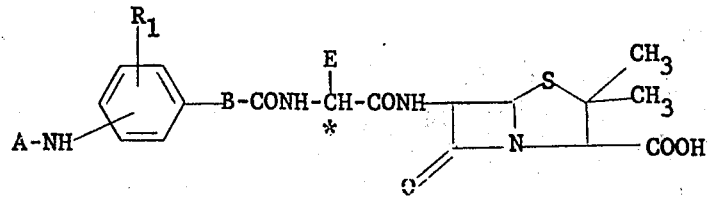

and the pharmaceutically acceptable nontoxic salts thereof wherein the carbon atom designated by * is asymmetrically substituted;

$R_1$ is hydrogen, halo, lower alkyl, hydroxy, nitro or A—NH—;

A is $R_3CO$— or $R_4CS$— in which
  $R_3$ is hydrogen; lower alkyl; halo(lower alkyl); cycloalkyl of 3 to 11 carbon atoms unsubstituted or substituted by hydroxy or alkyl of 1 or 2 carbon atoms; cycloalkenyl of 3 to 11 carbon atoms; bicycloalkyl of up to 8 carbon atoms; bicyloalkenyl of up to 8 carbon atoms; aryl of 6 to 10 carbon atoms, unsubstituted or substituted by from 1 to 3 substituents selected from the group consisting of alkyl of 1 to 4 carbon atoms, alkoxy of 1 to 4 carbon atoms, halo, trifluoromethyl, nitro, amino and alkylsulfonyl of 1 to 4 carbon atoms, or substituted by methylenedioxy, azidoaryl of 6 to 10 carbon atoms; azido(lower alkyl); amino; or thienyl; and
  $R_4$ is lower alkylamino or arylamino of 6 to 10 carbon atoms;

B is a direct bond or —CH=CH—; and

E is phenyl; phenyl substituted by hydroxy, azido, lower alkyl, lower alkoxy, lower alkylthio or chloro; or thienyl, in combination with a pharmaceutical carrier.

2. A composition according to claim 1 in which in said penicillin $R_1$ is hydrogen or hydroxy, A is $R_3CO$, B is a direct bond and E is phenyl, hydroxyphenyl or thienyl.

3. A composition according to claim 2 in which in said penicillin $R_3$ is hydrogen; lower alkyl; chloro(lower)alkyl; dichloro(lower)alkyl; bromo(lower)alkyl; dibromo(lower)alkyl; cycloalkyl of 3 to 7 carbon atoms; cycloalkenyl of 3 to 7 carbon atoms; norbornyl; unsubstituted phenyl; phenyl substituted by 1 to 3 substituents selected from the group consisting of methyl, ethyl, methoxy, ethoxy, chloro, bromo, fluoro, trifluoromethyl, nitro, amino, methylsulfonyl or ethylsulfonyl or substituted by methylenedioxy; amino; or thienyl.

4. A composition according to claim 3 in which in said penicillin $R_1$ is hydrogen, $R_3$ is hydrogen or cycloalkyl and E is phenyl.

5. A composition according to claim 1 wherein said compound is a salt of said penicillin selected from the group consisting of the sodium, potassium, magnesium, calcium, aluminum, ammonium, a di(lower alkyl)amine, a tri(lower alkyl) amine, procaine, dibenzylamine, N,N'-dibenzylethylenediamine, N-benzyl-β-phenylethylamine, N-methyl-morpholine, N-ethyl-morpholine, 1-ephenamine, dehydroabietylamine, N,N'-bis-dehydroabietylethylenediamine, and N-lower alkyl-piperidine salts.

6. A composition according to claim 1 wherein said penicillin is in the form of the sodium salt and the configuration about the carbon atom designated * is D.

7. A composition according to claim 1 in which said compound is D-α-(4-cyclopropane-carbonylamino-benzoylamino)-benzylpenicillin or the sodium salt thereof.

8. A composition according to claim 1 in which said compound is D-α-(4-cyclopentane-carbonylamino-benzoylamino)-benzylpenicillin or the sodium salt thereof.

9. A composition according to claim 1 in which said compound is D-α-(4-cycloheptane-carbonylamino-benzoylamino)-benzylpenicillin or the sodium salt thereof.

10. A composition according to claim 1 in which said compound is D-α-(4-cyclopentanecarbonylamino-2-hydroxybenzoylamino)-benzylpenicillin or the sodium salt thereof.

11. A composition according to claim 1 in which said compound is D-α-[4-(4-cycloheptane-1-carbonylamino)benzoyl-amino]-benzylpenicillin or the sodium salt thereof.

12. A composition according to claim 1 in which said compound is D-α-[4-(4-aminobenzoylamino)benzoylamino]-benzylpenicillin or the sodium salt thereof.

13. A composition according to claim 1 in which said compound is D-α-[4-(3,4,5-trimethoxybenzoylamino)-cinnamoyl-amino]-benzylpenicillin or the sodium salt thereof.

14. A composition according to claim 1 in which said compound is D-α-[4-(4-methylsulphonylbenzoylamino)benzoylamino]-benzylpenicillin or the sodium salt thereof.

15. A composition according to claim 1 in which said compound is D-α-(4-cyclopentanecarbonylaminobenzoylamino)-p-hydroxybenzylpenicillin or the sodium salt thereof.

16. A composition according to claim 1 in which said compound is D-α-(4-cyclopropanecarbonylamino-cinnamoylamino)-benzylpenicillin or the sodium salt thereof.

17. A composition according to claim 1 in which said compound is D-α-(4-cyclobutanecarbonylamino-cinnamoylamino)-benzylpenicillin or the sodium salt thereof.

18. A composition according to claim 1 in which said compound is D-α-(4-formylaminocinnamoylamino)-benzylpenicillin or the sodium salt thereof.

19. The method of combatting infections in animals and humans which comprises administering thereto an antibacterially effective amount of a compound selected from the group consisting of a penicillin of the formula:

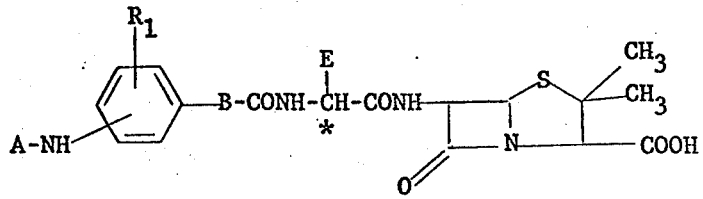

and the pharmaceutically acceptable nontoxic salts thereof wherein
the carbon atom designated by * is asymmetrically substituted;
$R_1$ is hydrogen, halo, lower alkyl, hydroxy, nitro or A—NH—;
A is $R_3CO$— or $R_4CS$— in which
$R_3$ is hydrogen; lower alkyl; halo(lower alkyl); cycloalkyl of 3 to 11 carbon atoms unsubstituted or substituted by hydroxy or alkyl of 1 or 2 carbon atoms; cycloalkenyl of 3 to 11 carbon atoms; bicycloalkyl of up to 8 carbon atoms; bicyloalkenyl of up to 8 carbon atoms; aryl of 6 to 10 carbon atoms, unsubstituted or substituted by from 1 to 3 substituents selected from the group consisting of alkyl of 1 to 4 carbon atoms, alkoxy of 1 to 4 carbon atoms, halo, trifluoromethyl, nitro, amino and alkylsulfonyl of 1 to 4 carbon atoms, or substituted by methylenedioxy, azidoaryl of 6 to 10 carbon atoms; azido(lower alkyl); amino; or thienyl; and
$R_4$ is lower alkylamino or arylamino of 6 to 10 carbon atoms;
B is a direct bond or —CH=CH—; and
E is phenyl; phenyl substituted by hydroxy, azido, lower alkyl, lower alkoxy, lower alkylthio or chloro; or thienyl.

20. A composition for use in promoting growth in animals which comprises at least a growth promoting amount of a compound selected from the group consisting of a penicillin of the formula:

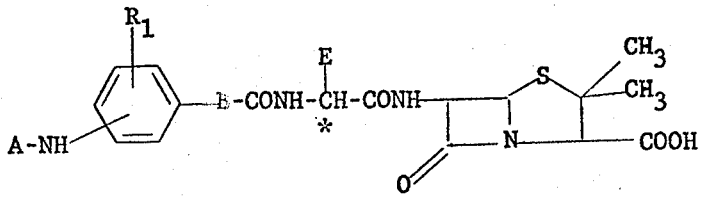

and the pharmaceutically acceptable nontoxic salts thereof wherein
the carbon atom designated by * is asymmetrically substituted;
$R_1$ is hydrogen, halo, lower alkyl, hydroxy, nitro or A—NH—;
A is $R_3CO$— or $R_4CS$— in which
$R_3$ is hydrogen; lower alkyl; halo(lower alkyl); cycloalkyl of 3 to 11 carbon atoms unsubstituted or substituted by hydroxy or alkyl of 1 or 2 carbon atoms; cycloalkenyl of 3 to 11 carbon atoms; bicycloalkyl of up to 8 carbon atoms; bicyloalkenyl of up to 8 carbon atoms; aryl of 6 to 10 carbon atoms, unsubstituted or substituted by from 1 to 3 substituents selected from the group consisting of alkyl of 1 to 4 carbon atoms, alkoxy of 1 to 4 carbon atoms, halo, trifluoromethyl, nitro, amino and alkylsulfonyl of 1 to 4 carbon atoms, or substituted by methylenedioxy, azidoaryl of 6 to 10 carbon atoms; azido(lower alkyl); amino; or thienyl; and
$R_4$ is lower alkylamino or arylamino of 6 to 10 carbon atoms;
B is a direct bond or —CH=CH—; and
E is phenyl; phenyl substituted by hydroxy, azido, lower alkyl, lower alkoxy, lower alkylthio or chloro; or thienyl, in combination with a nutritious carrier or animal drinking water.

21. The method of enhancing the growth of animals which comprises administering to said animals a growth promoting amount of a compound selected from the group consisting of a penicillin of the formula:

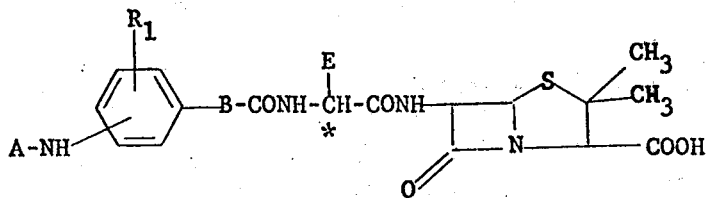

and the pharmaceutically acceptable nontoxic salts thereof wherein
the carbon atom designated by * is asymmetrically substituted;
$R_1$ is hydrogen, halo, lower alkyl, hydroxy, nitro or A—NH—;
A is $R_3CO$— or $R_4CS$— in which
  $R_3$ is hydrogen; lower alkyl; halo(lower alkyl); cycloalkyl of 3 to 11 carbon atoms unsubstituted or substituted by hydroxy or alkyl of 1 or 2 carbon atoms; cycloalkenyl of 3 to 11 carbon atoms; bicycloalkyl of up to 8 carbon atoms; bicyloalkenyl of up to 8 carbon atoms; aryl of 6 to 10 carbon atoms, unsubstituted or substituted by from 1 to 3 substituents selected from the group consisting of alkyl of 1 to 4 carbon atoms, alkoxy of 1 to 4 carbon atoms, halo, trifluoromethyl, nitro, amino and alkylsulfonyl of 1 to 4 carbon atoms, or substituted by methylenedioxy, azidoaryl of 6 to 10 carbon atoms; azido(lower alkyl); amino; or thienyl; and
  $R_4$ is lower alkylamino or arylamino of 6 to 10 carbon atoms;
B is a direct bond or —CH=CH—; and
E is phenyl; phenyl substituted by hydroxy, azido, lower alkyl, lower alkoxy, lower alkylthio or chloro; or thienyl.

* * * * *